(12) United States Patent
Yamamoto et al.

(10) Patent No.: US 6,741,731 B1
(45) Date of Patent: May 25, 2004

(54) SIDE SURFACE INSPECTING APPARATUS FOR TABLET, FRONT AND BACK SURFACE INSPECTING APPARATUS FOR TABLET, AND TABLET APPEARANCE INSPECTING APPARATUS USING THE SAME

(75) Inventors: Taizo Yamamoto, Osaka (JP); Motohiro Yagyu, Nara-ken (JP)

(73) Assignee: Shionogi Qualicaps Co., Ltd., Nara-Ken (JP)

( * ) Notice: Subject to any disclaimer, the term of this patent is extended or adjusted under 35 U.S.C. 154(b) by 489 days.

(21) Appl. No.: 09/621,626

(22) Filed: Jul. 21, 2000

(30) Foreign Application Priority Data

Jul. 23, 1999 (JP) .......................................... 11-209920

(51) Int. Cl.⁷ ................................................ G06K 9/00
(52) U.S. Cl. ...................................... 382/141; 23/865.8
(58) Field of Search ................................ 382/141, 100; 73/865.8, 863.45, 863.92, 864.62, 800; 356/237.2, 237.3, 237.1; 348/89, 92, 125, 128

(56) References Cited

U.S. PATENT DOCUMENTS

| | | | | |
|---|---|---|---|---|
| 3,709,598 A | * | 1/1973 | Vandenberg et al. | ........ 356/198 |
| 4,757,382 A | | 7/1988 | Kaziura et al. | ............. 358/101 |
| 5,085,510 A | * | 2/1992 | Mitchell | ...................... 356/237 |
| 5,661,249 A | * | 8/1997 | Rupp et al. | ................. 73/865.8 |
| 6,079,284 A | * | 6/2000 | Yamamoto et al. | ........ 73/865.8 |

FOREIGN PATENT DOCUMENTS

| | | |
|---|---|---|
| EP | 172663 A2 | 7/1985 |
| EP | 859227 A2 | 2/1998 |
| GB | 937612 A | 9/1963 |
| WO | 9301006 | 5/1992 |

OTHER PUBLICATIONS

Kajiura, Toshihiro, "Automating Video Tablet Inspection," *Pharmaceutical Technology*, No. 4, Apr. 13, 1989.
Patent Abstracts of Japan, JP 01 320454, vol. 14, No. 128, Mar. 9, 1990.
Patent Abstracts of Japan, JP 11 051873, vol. 1999, No. 5, May 31, 1999.

* cited by examiner

*Primary Examiner*—Yon J. Couso
(74) *Attorney, Agent, or Firm*—Birch, Stewart, Kolasch & Birch, LLP

(57) ABSTRACT

An apparatus for inspecting the side surfaces of tablets is configured such that images of the side surfaces of tablets are picked up by making the tablets held in holding pockets of an outer cylinder roll on a continuously rotating inner cylinder and thereby rotate on their axes, whereby the images of the side surfaces of the tablets can be picked up in a state in which the tablets stably rotate on their axes in upright states, so that the side surfaces of the tablets can be easily, accurately inspected. An apparatus for inspecting the front and back surfaces of tablets is configured such that the tablets in a tablet storing portion are introduced in tablet feed passages of a vibration plate, being moved to one end portion of the vibration plate, and are fed from the one end portion of the vibration plate onto a front surface inspecting drum, whereby the postures of the tablets are controlled in falling-down states suitable for front and back surface inspection without applying large loads or impacts to the tablets. A tablet appearance inspecting apparatus including the side surface inspecting apparatus and the front and back surface inspecting apparatus is also disposed.

20 Claims, 17 Drawing Sheets

SIDE SURFACE INSPECTING APPARATUS FOR TABLET, FRONT AND BACK SURFACE INSPECTING APPARATUS FOR TABLET, AND TABLET APPEARANCE INSPECTING APPARATUS USING THE SAME

BACKGROUND OF THE INVENTION

The present invention relates to an apparatus for inspecting side surfaces of tablets, which is used for carrying flat-shaped tablets in upright states with the diameter direction thereof directed in the vertical direction, photographing the tablets in the course of carrying operation, and detecting, on the basis of the images thus obtained, appearance defects on the.side surfaces, for example, adhesion of foreign matters and contamination, cracks and chips, and deformation; an apparatus for inspecting front and back surfaces of tablets, which is used for carrying the tablets in the falling-down states with the thickness direction thereof directed in the vertical direction, turning over the tablets in the course of carrying operation, photographing the tablets before and after turn-over, and detecting the above-described appearance defects on the basis of images of the front and back surfaces of the tablets obtained by photographing; and a tablet appearance inspecting apparatus for inspecting the side surfaces and front and back surfaces of tablets while carrying the tablets by using the side surface inspecting apparatus and the front and back surface inspecting apparatus.

Conventionally, appearance defects on tablets, for example, adhesion of foreign matters or contamination, cracks or chips, deformation, and printing failure have been automatically inspected by an appearance inspecting apparatus. In the case of automatically inspecting flat-shaped tablets by using such an appearance inspecting apparatus, there has been generally adopted a method of carrying the tablets in upright states with the diameter direction thereof directed in the vertical direction; photographing, in the course of carrying operation, the tablets by using a camera, thereby picking up images of the side surfaces of the tablets: changing the postures of the tablets into falling-down states with the thickness direction thereof directed in the vertical direction and carrying the tablets in the falling-down state; turning over the tablets in the course of carrying operation; photographing the tablets before and after turn-over by using a camera, thereby picking up images of the front and back surfaces of the tablets; and processing the images of the side surfaces and front and back surfaces of the tablets, thereby detecting the presence or absence of the above-described defects.

One example of such an appearance inspecting apparatus is shown in FIG. 14.

The appearance inspecting apparatus includes a tablet feed unit p1 for carrying a number of flat-shaped tablets (hereinafter, referred to simply as "tablets") stored in a hopper p11 to an inspection mechanism portion; a side surface inspecting unit p2 having a side surface inspecting drum p21 and a side surface image pickup device p22; a posture change unit p3 having a posture change drum p31; a front and back surface inspecting unit p4 having a front surface inspecting drum p41, a back surface inspecting drum p42, a front surface image pickup device p43, and a back surface image pickup device p44; a separating unit p5 having a separating drum p51, a non-defective recovery conveyor p52, and a defective recovery can p53: and a decision unit (not shown) for processing images picked up by the three image pickup devices p22, p43, and p44, and detecting the presence or absence of appearance defects. In FIG. 14, reference numerals p221, p431, and p441 designate cameras, and p222, p432, and p442 designate illuminating devices.

The appearance inspection by using the above appearance inspecting apparatus is performed in accordance with the following procedure:

(1) A number of tablets are fed at random from the hopper p11 to the tablet feed unit p1, at which the postures of the tablets are changed into upright states with the diameter direction thereof directed in the vertical direction (hereinafter, referred to as simply "upright states"), and the tablets in the upright states are continuously fed from the tablet feed unit p1 to the side surface inspecting drum p21 of the side surface inspecting unit p2.

(2) The upright tablets held in holding pockets of the side surface inspecting drum p21 are carried downwardly by the rotation of the drum p21, and in the course of carrying operation, the tablets are made to rotate on their axes in the holding pockets and simultaneously photographed by the side surface image pickup device p22. In this way, images of the all-round side surfaces of the tablets are picked up by the side surface image pickup device p22.

(3) The tablets are transferred to the posture change drum p31 of the posture change unit p3, at which the upright tablets are fallen in the horizontal direction into falling-down states with the thickness direction thereof directed in the vertical direction (hereinafter, referred to simply as "falling-down states"), and the tablets in the falling-down states are delivered to the front surface inspecting drum p41 of the front and back surface inspecting unit p4.

(4) The tablets held in the falling-down states in tablet holding pockets formed in the surface of the front surface inspecting drum p41 are carried downwardly by the rotation of the drum p41, and in the course of carrying operation, the tablets are photographed by the front surface image pickup device p43. In this way, the images of the front surfaces of the tablets are picked up by the front surface image pickup device p43.

(5) The tablets are delivered to the back surface inspecting drum p42, being turned over, and are held in the falling-down state in tablet holding pockets of the back surface inspecting drum p42. The tablets in the falling-down states are then carried downwardly by the rotation of the drum p42, and in the course of carrying operation, the tablets are photographed by the back surface image pickup device p44. In this way, the images of the back surfaces of the tablets are picked up by the back surface image pickup device p44.

(6) The tablets are transferred to the separating drum p51 of the separating unit p5, and on the basis of the inspection result obtained by processing the images of the side surfaces and front and back surfaces of the tablets, defective tablets are transferred to the defective recovery can p53, and non-defective tablets are transferred to the non-defective recovery conveyor p52 to be recovered in a recovery container "c".

The above appearance inspecting apparatus, however, often fails to stably pick up images of side surfaces of tablets by the side surface inspecting unit p2.

To be more specific, the side surface inspecting drum p21 of the side surface inspecting unit p2 includes, as shown in FIG. 15, an inner cylinder p211 and an outer cylinder p212 rotatably disposed on the outer peripheral side of the inner cylinder p211. A roller p213 rotatable on its axis is disposed inside the inner cylinder p211 in a state in which the peripheral surface thereof is exposed to the outer peripheral surface of the inner cylinder p211 through a through-window provided in the inner cylinder p211. On the other hand, as shown in FIG. 16, a number of through-hole shaped holding pockets p214 are aligned in the peripheral surface of the outer cylinder p212. The pickup of an image of the side surface of each tablet is performed by the side surface inspecting unit p2 as follows: namely, as shown in FIG. 15, the tablet "t" held in the upright state in the holding pocket p214 of the outer cylinder p212 is carried by intermittent rotation of the outer cylinder p212 while rolling on the outer peripheral surface of the inner cylinder p211; and when carried on the roller p213 rotating on its axis and intermittently stopped, the tablet "t" rotates on its axis in the state being stopped in the upright posture by the rotation of the roller p213, and in such a state, the tablet "t" is photographed by the image pickup device p22.

In this case, when carried on the roller p213 by the rotation of the outer cylinder p212, the tablet "t" rolling on the inner peripheral surface of the inner cylinder p211 is raised on the roller p213 projecting from the outer peripheral surface of the inner cylinder p211, and in such a state, the tablet "t" rotates on their axes by the rotation of the roller p213. As a result, the posture of the tablet "t" upon rotation thereof on its axis is unstable, tending to cause an inconvenience that the tablet "t" is not necessarily allowed to stably rotate on its axis. Further, since the tablet "t" having slowly rolled on the fixed inner cylinder p211 is suddenly landed on the roller p213 rotating on its axis at a high speed and is rapidly rotated by the rotation of the roller p213 at a high speed, it takes a slight time until the rotation of the tablet "t" on its axis becomes stable, and since the tablet "t" rotates on its axis while rolling on the small-sized roller p213 rotating on its axis at a high speed, the tablet "t" may be slightly jumped from the roller p213, thereby making it difficult for the table "t" to rotate on its axis while keeping its stable posture.

The prior art tablet appearance inspecting apparatus, therefore, is not easy to obtain a clear image of the side surface of the tablet "t" which rotates on its axis as described.

Another problem of the prior art tablet appearance inspecting apparatus will be described below. According to the prior art apparatus, the posture of the tablet "t" is changed by a manner of feeding the tablet "t" in an upright state from the side surface inspecting drum p21 in a posture change pocket formed in the outer peripheral surface of the posture change drum p31; and making the tablet "t" fall down by a guide plate to change the posture of the tablet "t" from the upright state to a falling-down state in the course of carrying operation by the rotation of the posture change drum p31. Accordingly, a large load or impact is applied to the tablet "t" upon the above-described posture change operation, with a result that the tablet "t" is susceptible to breakage such as cracks or chips upon the posture change thereof.

To be more specific, as shown in FIG. 17, the posture change of the tablet "t" by the posture change drum p31 is performed as follows: The tablet "t" in an upright state is fed from the side surface inspecting drum p21 into a posture change pocket p311 of the posture change drum p31, and is carried downwardly, by the rotation of the posture change drum p31, in a state in which part of the tablet "t" projects from the posture change pocket p311. At this time, the tablet "t" is prevented from being dropped from the posture pocket p311 by a guide plate P32 fixed along the outer peripheral surface of the posture change drum p31, and the projecting portion of the tablet "t" is made to enter an approximately V-shaped posture change groove p321 obliquely tilted with respect to the rotational direction by only an edge portion p322 provided on one side of the guide plate p32, to push sideways the projecting portion of the tablet "t" by the tilting edge portion p322 of the posture change groove p321, thereby pushing down the tablet "t" in the posture change pocket p311 to change the posture of the tablet "t" into a falling-down posture.

In this way, according to the prior art tablet appearance inspecting apparatus, in the course of carrying the tablet "t" held on the peripheral surface of the posture change drum p31 by the rotation of the posture change drum p31, the upright tablet "t" is slid in contact with the posture change groove p321 of the guide plate p32, to be forcibly pushed down by the tilting edge portion p322 of the posture change groove p321, and accordingly, a large load or impact is applied to the tablet "t" upon the posture change thereof. As a result, a relatively brittle tablet may cause breakage such as cracks or chips. Also since the tablet "t" must enter the posture change groove p321 while keeping a stable upright posture, if the upright posture of the tablet "t" is unstable, the tablet "t" may be jammed between the guide plate p32 and the outer peripheral surface of the posture change drum p31, with a result that the tablet "t" may cause cracks.

Further, the size of the posture change pocket p311 formed in the posture change drum p31 must be set at a suitable value depending on the size and shape of the tablets "t" for stably changing the postures of the tablets "t", and accordingly, each time the kind (size or thickness) of tablets to be inspected is changed, the posture change drum p31 must be changed to the posture change drum having the posture change pocket p311 of the size corresponding to the kind of the tablets. This requires significantly complicated works to change the kind of tablets to be inspected.

SUMMARY OF THE INVENTION

An object of the present invention is to provide an apparatus for inspecting the side surfaces of tablets, which is capable of picking up images of the side surfaces of the tablets while making the tablets stably rotate on their axes in upright states, thereby easily, accurately inspecting the side surfaces of the tablets; an apparatus for inspecting front and back surfaces of tablets, which is capable of inspecting the front and back surfaces of the tablets by controlling the postures of the tablets into falling-down postures without applying large loads or impacts on the tablets; and a tablet appearance inspecting apparatus for inspecting side surfaces and front and back surfaces of tablets while carrying the tablets by using the side surface inspecting apparatus and the front and back surface inspecting apparatus.

To achieve the above object, according to the present invention, there is provided an apparatus for inspecting side surfaces of tablets, including:

an inner cylinder continuously rotatable at a specific speed;

an outer cylinder disposed on the outer peripheral side of the inner cylinder in such a manner as to be intermittently rotatable along the outer peripheral surface of the inner cylinder, the outer cylinder having in its peripheral wall a number of through-hole shaped holding pockets; and a side surface image pickup device for photographing tablets held in the holding pockets of the outer cylinder, thereby picking up images of the side surfaces of the tablets;

wherein the inspecting apparatus inspects the side surfaces of flat-shaped tablets by holding the tablets, which are in upright states with the diameter direction thereof directed in the vertical direction, in the holding pockets of the outer cylinder intermittently rotating; carrying the tablets by the intermittent rotation of the outer cylinder while making the tablets roll on the outer peripheral surface of the inner cylinder continuously rotating; making, when the outer cylinder is intermittently stopped in the course of carrying operation, the tablets rotate on their axes in the holding pockets by the continuous rotation of the inner cylinder, and photographing the tablets by the side surface image pickup device thereby picking up images of the all-round side surfaces of the tablets; and processing the images thus obtained, thereby detecting the presence or absence of appearance defects on the side surfaces of the tablets.

That is to say, the side surface inspecting apparatus of the present invention includes the intermittent rotatable outer cylinder for carrying tablets held in the holding pockets and the continuously rotatable inner cylinder inside the outer cylinder, wherein the tablets held in the upright states in the holding pockets of the outer cylinder are carried while rolling on the outer peripheral surface of the inner cylinder by the intermittent rotation of the outer cylinder, and at a specific carrying point, the tablets rotating on their axes in the holding pockets of the intermittently stopped outer cylinder while rolling on the outer peripheral surface of the continuously rotating inner cylinder are photographed by the side surface image pickup device. In this way, the images of the side surfaces of the tablets are picked up by the side surface image pickup device.

Accordingly, even in either the carrying state or the side surface image pickup state, the tablets rotate on their axes while rolling on the outer peripheral surface of the inner cylinder. As a result, unlike the prior art apparatus in which the tablets upon photographing are made to rotate on their axes by a separately provided roller rotatable on its axis, the tablets upon photograph can be made to rotate on their axes in the same state as that upon carrying of the tablets without the occurrence of the inconvenience that the tablets are raised on the roller rotatable on its axis. Further, as compared with the prior art apparatus in which the tablets are moved from the fixed inner cylinder to the roller rotating on its axis at a high speed and thereby the rotational speed is rapidly increased, the tablets can be significantly smoothly shifted to the rotational states on their axes suitable for photographing, whereby images of the side surfaces of the tablets stably rotating on their axes can be picked up. Further, since the inner cylinder for making the tablets rotate on their axes upon photographing of the sides surfaces of the tablets has a diameter much larger than the diameter of the prior art roller rotatable on its axis, the tablets upon photographing rotate on their axes while rolling on the outer peripheral surface, which is flatter than the outer peripheral surface of the above roller, of the inner cylinder. In this regard, the rotation of the tablets on their axes becomes further stable.

In this way, according to the side surface inspecting apparatus of the present invention, as compared with the prior art apparatus characterized by making tablets roll on their axes by using the roller rotatable on their axes, it is possible to pick up images of the side surfaces of tablets while making the tablets stably rotate on their axes, and hence to certainly obtain clear images of the side surfaces of the tablets and thereby accurately inspect the side surfaces of the tablets.

To achieve the above object, according to the present invention, there is also provided an apparatus for inspecting front and back surfaces of tablets including:

a front surface inspecting drum for holding flat-shaped tablets, which are in falling-down states with the thickness direction thereof directed in the vertical direction, on the outer peripheral surface thereof, and carrying the tablets by the rotation of the drum at a specific speed;

a back surface inspecting drum, disposed in a state in which the outer peripheral surface thereof is in proximity to the outer peripheral surface of the front surface inspecting drum, for receiving the tablets from the front surface inspecting drum in a state in which the tablets are turned over, holding the tablets, which are in the falling-down states, on the outer peripheral surface thereof, and carrying the tablets by rotation of the drum at a specific speed;

a front surface image pickup device for photographing the tablets held on the outer peripheral surface of the front surface inspecting drum, thereby picking up images of the front surfaces of the tablets;

a back surface image pickup device for photographing the tablets held on the outer peripheral surface of the back surface inspecting drum, thereby picking up images of the back surfaces of the tablets; and tablet feed unit for feeding the tablets onto the outer peripheral surface of the front surface inspecting drum, the tablet feed unit comprising: a vibration plate having tablet feed passages each having a size allowing a tablet in the falling-down state to pass therethrough, the vibration plate being tilted downwardly to the front inspecting drum by a specific angle with one end of the vibration plate positioned in proximity to the outer peripheral surface of the front surface inspecting drum; and a tablet storing portion for storing a specific amount of tablets, the tablet storing portion being provided on the other end side of the vibration plate, whereby the tablets in the tablet storing portion are continuously introduced in the tablet feed passages of the vibration plate, and the tablets thus introduced in the tablet feed passages are continuously moved, by fine vibration of the vibration plate, to the one end portion of the vibration plate and fed from the one end portion of the vibration plate onto the front surface inspecting drum;

wherein each of the front surface inspecting drum and the back surface inspecting drum includes a suction groove formed in the outer peripheral surface thereof in such a manner as to extend along the circumferential direction, a number of suction holes formed in the suction grooves in such a manner as to align in the circumferential direction, and at least a pair of rubber rings mounted on both side edge portions of the suction groove with the suction holes put therebetween, whereby the tablets are attractively held while lying astride the pair of the rubber rings by a suction force obtained by sucking the inside of the suction groove from the inside of the drum through the suction holes.

The front and back surface inspecting apparatus of the present invention is intended to attractively hold tablets in falling-down states, by suction, on the rubber rings disposed on the outer peripheral surface of the front surface inspecting drum or back surface inspecting drum; and turn over the tablets by delivery of the tablets between the front surface inspecting drum and the back surface inspecting drum, and in the course of carrying operation, photograph the tablets on the front surface inspecting drum and the tablets on the back surface inspecting drum, to pick up images of the front and back surfaces of the tablets, thereby inspecting the front and back surfaces of the tablets. In this case, according to the apparatus of the present invention, the tablets stored in the tablet storing portion are introduced in the tablet feed passages of the vibration plate, and moved to one end portion of the vibration plate disposed in proximity to the outer peripheral surface of the front surface inspecting drum by fine vibration of the vibration plate. At this time, since each of the tablet feed passages has a size allowing a tablet in a falling-down state to pass therethrough, the tablets in the tablet feed passages are certainly allowed to be in falling-down states by vibration of the vibration plate. The tablets in the falling-down states are moved from the one end portion of the vibration plate to the front surface inspecting drum, to be thus fed on the front surface inspecting drum in the falling-down states.

Accordingly, it is not required to perform any special operation to change the postures of the tablets having been subjected to side surface inspection by the side surface inspecting drum from upright states to falling-down states, for example, by charging the non-defective tablets having no appearance defects on the side surfaces, which have been inspected by the side surface inspecting apparatus, in the tablet storing portion; feeding the tablets to the front surface inspecting drum by the vibration plate; turning over the tablets by delivery of the tablets between the front surface inspecting drum and the back surface inspecting drum and carrying the tablets thus turned over, and picking up, in the course of carrying operation, images of the side surfaces and front and back surfaces of the tablets, thereby inspecting the side surfaces and front and back surfaces of the tablets. That is to say, the front and back surfaces of tablets can be inspected only by feeding the tablets, which have been subjected to side surface inspection, in the tablet storing portion of the front surface inspecting drum.

As a result, according to the front and back surface inspecting apparatus of the present invention, as compared with the prior art apparatus characterized by inspecting front and back surfaces of tablets by forcibly changing the postures of the tablets from upright postures to falling-down postures, it is possible to certainly inspect the front and back surfaces of tablets by significantly reducing loads or impacts applied to the tablets without occurrence of cracking, chipping, or shaving.

Further, according to the front and back surface inspecting apparatus of the present invention, since tablets are attracted on the rubber rings mounted on the outer peripheral surface of the front surface inspecting drum or back surface inspecting drum to be held thereon while projecting from the outer peripheral surface of the drum, the tablets can be photographed without occurrence of any shadow on the tablets. Since the tablets are photographed in a state in which the tablets are attractively held on the surface of the drum without no gap therebetween, it is possible to certainly obtain clear images, and hence to accurately inspect the front and back surfaces of the tablets. Further, since tablets are turned over, by delivery of the tablets between the front surface inspecting drum and the back surface inspecting drum, in a state in which the tablets are put between the rubber rings on the front surface inspecting drum and the rubber rings on the back surface inspecting drum, it is possible to certainly deliver the tablets between both the drums without applying large loads to the tablets so much by the effect of the elasticity and deflection of the rubber rings, and hence to certainly perform the delivery and turn-over works of the tablets without occurrence of breakage of the tablets.

According to the front and back surface inspecting apparatus, since tablets are carried while being attractively held between both edges of a pair of the rubber rings, even if the size of the tablets is changed, such tablets can be carried while being attractively held on the same inspecting drum with no problem. Further, since the tablets are delivered between the front surface inspecting drum and the back surface inspecting drum in a state being put between the rubber rings by making use of the elasticity and deflection of the rubber rings, even if the thickness of the tablets is changed, such tablets can be delivered between both the drums without occurrence of breakage because the change in thickness of the tablets is permitted by the elasticity and deflection of the rubber rings. As a result, the front and back surface inspecting apparatus allows a change in size of tablets to be inspected, and each of the tablet feed passages provided in the vibration plate for feeding tablets onto the front surface inspecting drum may be designed into a size which allows one row of tablets in falling-down states to pass therethrough but does not allow two rows of tables in falling-down states to pass therethrough. In other words, even if the size of the tablets is somewhat changed, the tablets can be desirably fed by using the same vibration plate. As a result, it is possible to inspect tablets different in size (diameter or thickness) without the need of changing the front surface inspecting drum, back surface inspecting drum, and vibration plate.

Here, the front and back surface inspecting apparatus of the present invention may be configured, while not particularly limited thereto, such that the tablet feed unit further includes a tablet feed roller rotatable at a desired speed, the roller being disposed at the one end of the vibration plate in such a manner as to be in contact with or in proximity to the tablet feed passages, whereby the tablets are moved from the one end portion of the vibration plate onto the front surface inspecting drum by the rotation of the tablet feed roller, to be thereby fed at a desired speed.

To be more specific, by moving the tablets from the tablet storing portion to the one end of the vibration plate via the tablet feed passages, and further moving the tablets from the one end portion of the vibration plate onto the front surface inspecting drum by the tablet feed roller, thereby feeding the tablets onto the front surface inspecting drum, the tablets can be stably fed onto the front surface inspecting drum at a specific speed corresponding to the rotational speed of the tablet feed roller. As a result, it is possible to stably inspect the front and back surfaces of the tablets.

The feed speed of the tablets onto the front surface inspecting drum can be adjusted by controlling the rotational speed of the tablet feed roller. As a result, the feed speed of the tablets can be set at an optimum value in consideration of the size of the tablets, the feed speed of the tablets in the tablet storing portion, the required processing ability, the image pickup ability, and the ability of processing the pickup image. Even in this regard, it is possible to efficiently perform the accurate, stable inspect of the front and back surfaces of tablets.

To achieve the above object, according to the present invention, there is provided a tablet appearance inspecting apparatus for inspecting the side surfaces and front and back surfaces of tablets, which includes a side surface inspecting unit composed of the above-described side surface inspecting apparatus, particularly characterized by including a defective ejecting mechanism for selectively ejecting, in the course of carrying operation, the tablets carried while being held in the holding pockets of the outer cylinder, and a side surface defective decision unit for processing images of the side surfaces of the tablets, thereby deciding the presence or absence of appearance defects, wherein the tablets, which are decided as defective tablets each having an appearance defect on the side surface by the side surface defective decision unit, are selectively ejected from the holding pockets by the defective ejecting mechanism; and a front and back surface inspecting unit composed of the above-described front and back surface inspecting apparatus, particularly, characterized by including a defective ejecting mechanism for selectively ejecting, in the course of carrying operation, the tablets carried while being held on the outer peripheral surface of the back surface inspecting drum, and a front and back surface defective decision unit for processing images of the front and back surfaces of the tablets picked up by the front surface image pickup device and the back surface image pickup device, thereby deciding the presence or absence of appearance defects, wherein the tablets, which are decided as defective tablets each having an appearance defect on the front surface and/or back surface by the front and back surface defective decision unit, are selectively ejected from the back surface inspecting drum by the defective ejecting mechanism.

That is to say, the tablet appearance inspecting apparatus of the present invention is operated to inspect side surfaces of tablets by the side surface inspecting unit and selectively eject defective tablets each having an appearance defect on the side surface; feed all of the tablets with no defects on the side surfaces from the side surface inspecting drum into the tablet storing portion of the front and back inspecting unit; inspect front and back surfaces of the tablets by the front and back surface inspecting unit and selectively eject defective tablets each having an appearance defect on the front or back surface; and recover non-defective tablets with no appearance defects on the side surfaces and front and back surfaces from the back surface inspecting drum of the front and back surface inspecting unit.

Alternately, the tablet appearance inspecting apparatus of the present invention may be operated to feed tablets to be inspected in the tablet storing portion of the front and back surface inspecting unit; inspect the front and back surfaces of the tablets by the front and back surface inspecting unit, and selectively eject defective tablets each having an appearance defect on the front or back surface; change the postures of all of the tablets with no appearance defects on the front and back surfaces from the falling-down postures to right postures, and feed the tablets from the back surface inspecting drum of the front and back surface inspecting unit onto the side surface inspecting drum of the side surface inspecting unit; inspect the side surfaces of the tablets by the side surface inspecting unit and selectively eject defective tablets each having an appearance defect on the side surface; and recover non-defective tablets with no appearance defects on the side surfaces and front and back surfaces from the side surface inspecting drum of the side surface inspecting unit.

According to the above-described tablet appearance inspecting apparatus, it is possible to pick up images of the side surfaces of tables while making the tablets stably rotate on their axes in upright states and thereby certainly, accurately inspect the side surfaces of the tablets on the basis of the clear images of the side surfaces of the tablets, to inspect the front and back surfaces of the tablets in falling-down states without applying large loads or impacts to the tablets and thereby certainly inspect the front and back surfaces of the tablets without occurrence of breakage of the tablets, and to inspect tablets different in size (diameter or thickness) without the need of changing the front surface inspecting drum, back surface inspecting drum, and vibration plate of the front and back surface inspecting unit.

In the case of the inspecting operation of inspecting the front and back surfaces of tablets by the front and back surface inspecting unit, ejecting defective tablets having appearance defects on the front and back surfaces, inspecting the side surfaces of non-detective tablets with no appearance defects on the front and back surfaces, and ejecting defective tablets with appearance defects on the side surfaces, it is possible to eject the defective tablets being deformed by cracks or chips by the initial front and back surface inspection, and hence to certainly prevent the occurrence of an inconvenience that the tablets thus deformed are jammed in the holding pockets of the side surface inspecting drum upon side surface inspection by the side surface inspecting unit. This makes it possible to stably inspect the appearances of tablets.

DETAILED DESCRIPTION OF THE PREFERRED EMBODIMENTS

Hereinafter, embodiments of the present invention will be described with reference to the drawings.

Figure 1:
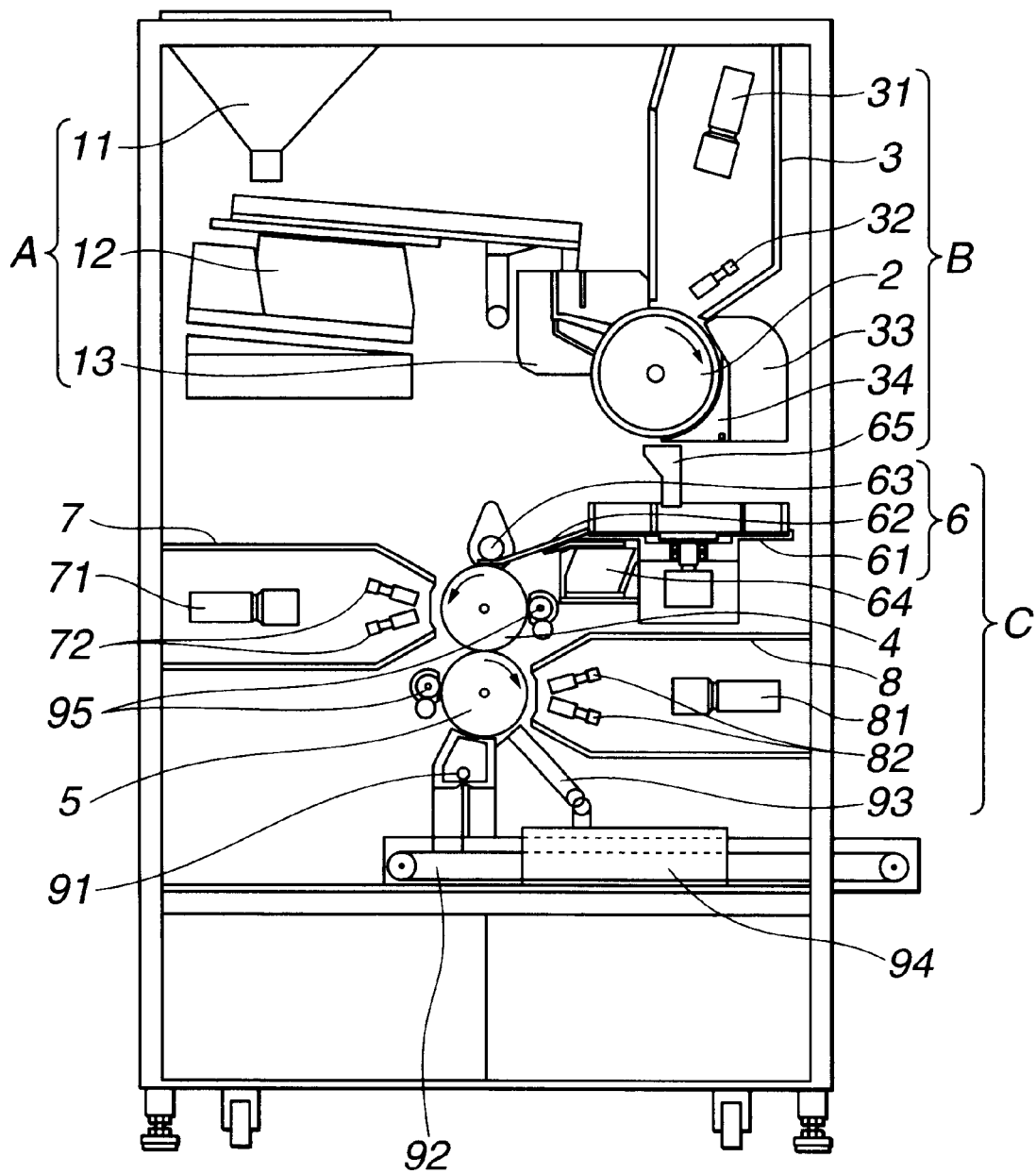
FIG. 1 is a schematic view showing a tablet appearance inspecting apparatus including a side surface inspecting apparatus and a front and back surface inspecting apparatus according to one embodiment of the present invention.

FIG. 1 shows a tablet appearance inspecting apparatus including a side surface inspecting apparatus and a front and back surface inspecting apparatus according to one embodiment of the present invention. The tablet appearance inspecting apparatus is used to inspect side surfaces of substances to be detected, typically, tablets continuously fed from a tablet feed unit A by a side surface inspecting unit B composed of the side surface inspecting apparatus of the present invention, and inspect front and back surfaces of the tablets fed from the side surface inspecting unit B by a front and back surface inspecting unit C composed of the front and back surface inspecting apparatus of the present invention.

As shown in FIG. 1, the tablet feed unit A includes a hopper 11 for feeding tablets to be inspected in the tablet appearance inspecting apparatus; a vibration feeder 12 for feeding the tablets continuously fed from the hopper 11 to the subsequent inspection mechanism portion at a specific speed; and an aligning-and-feeding device 13 for controlling the postures of the tablets fed from the vibration feeder 12 into upright postures and feeding the upright tablets to a side surface inspecting drum 2 of the side surface inspecting unit B.

While not shown, the aligning-and-feeding device 13 includes a plurality of rows of alignment grooves each having such a width as to allow only an upright tablet to enter the groove, and vibrators disposed on the upper ends of the alignment grooves. The tablets fed from the vibration feeder 12 to the alignment-and-feeding device 13 are raised into upright postures by vibration of the vibrators, and the upright tablets enter the alignment grooves, which tablets are then fed in the upright states to the outer peripheral surface of the side surface inspecting drum 2.

The side surface inspecting unit B is, as described above, composed the side surface inspecting apparatus according the embodiment of the present invention. As shown in FIG. 1, the side surface inspecting unit B includes the side surface inspecting drum 2 which rotates while holding tablets in the upright postures; a side surface image pickup device 3 having a camera 31 and an illuminating device 32; and a defective recovery can 33.

Figure 2:
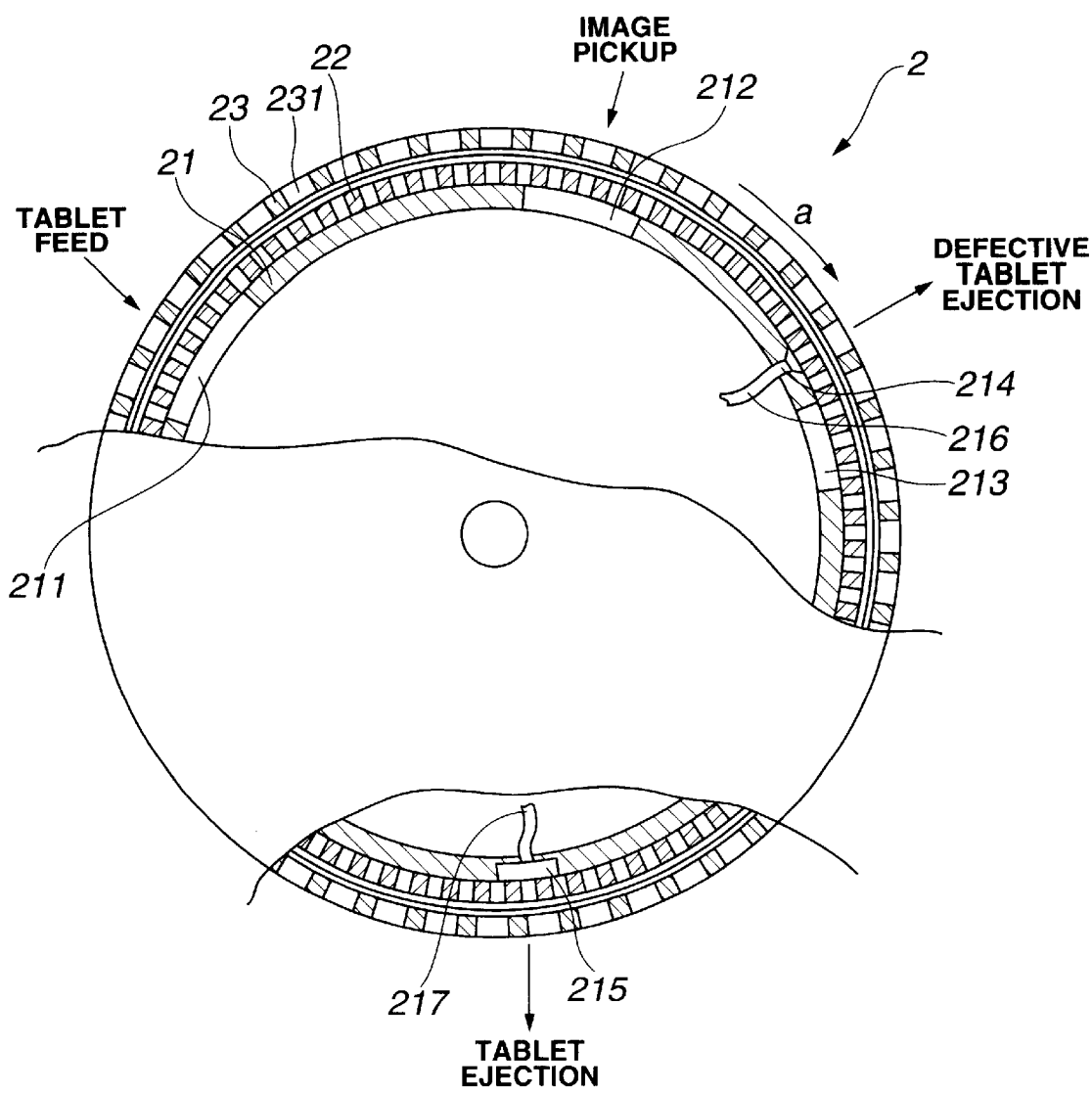
FIG. 2 is a schematic view, with parts partially cutaway, showing a side surface inspecting drum of the side surface inspecting apparatus.
Figure 3:
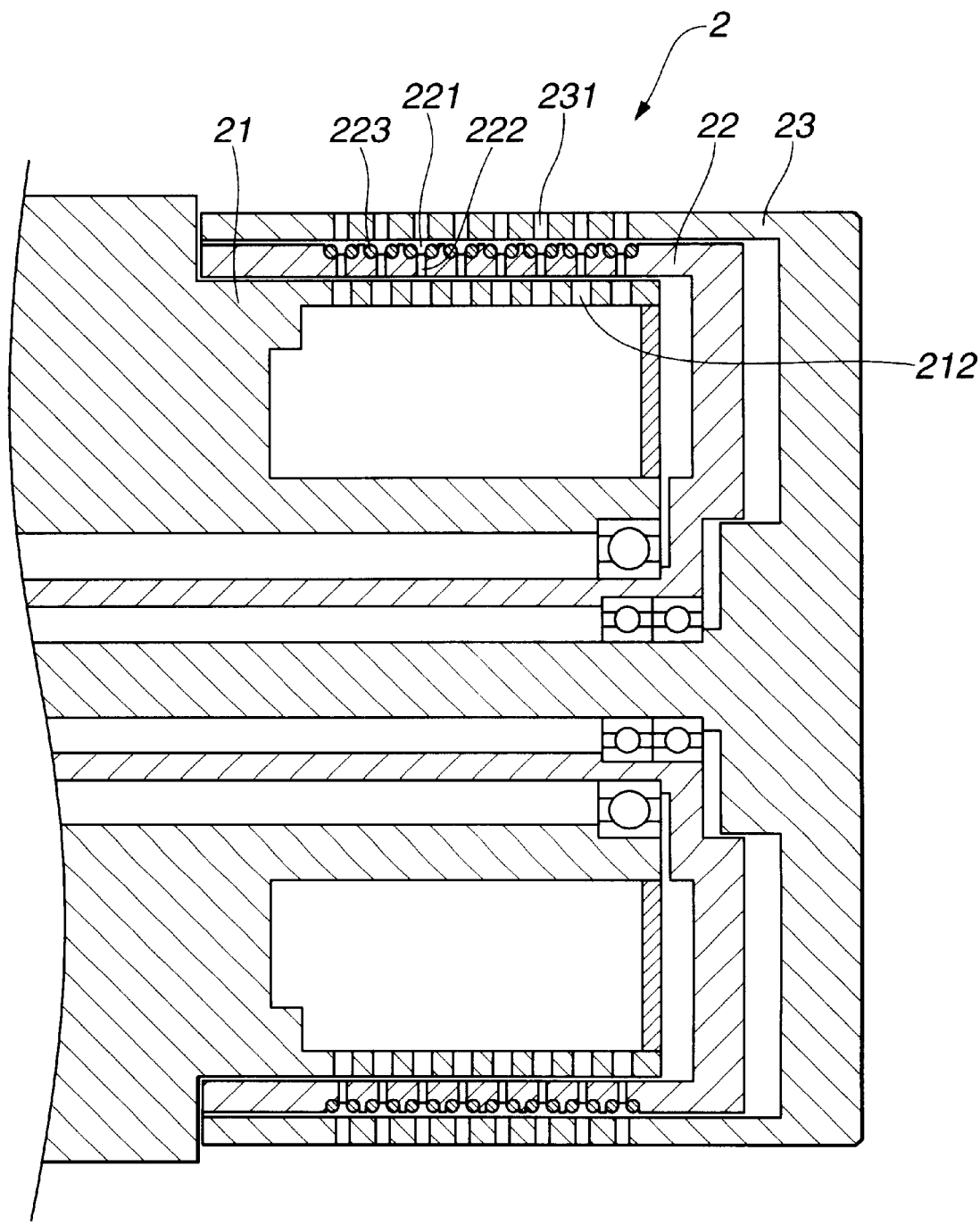
FIG. 3 is a sectional view of the side surface inspecting drum.

As shown in FIGS. 2 and 3, the side surface inspecting drum 2 includes a fixed shaft cylinder 21, an inner cylinder 22 rotatably disposed on the outer peripheral side of the shaft cylinder 21, and an outer cylinder 23 rotatably disposed on the outer peripheral side of the inner cylinder 22. The inner cylinder 22 is continuously rotatable clockwise (in the direction "a") in FIG. 2 along the outer peripheral surface of the shaft cylinder 21 at a specific speed. The outer cylinder 23 is intermittently rotatable clockwise (in the direction "a") in FIG. 2 along the outer peripheral surface of the continuously rotating inner cylinder 22 at a specific speed.

The outer peripheral surface of the outer cylinder 23 has a plurality of rows (eight rows in this embodiment) each of which is composed of a number of through-hole shaped holding pockets 231 aligned in the circumferential direction. The outer peripheral surface of the inner cylinder 22 has rail grooves 221 formed along the circumferential direction in such a manner as to correspond to the rows of the holding pockets 231 of the outer cylinder 23. A number of through-holes 222 are formed in each rail groove 221 in a state being aligned along the circumferential direction. A pair of rubber rings 223, each of which is formed into a circular shape in cross-section, are mounted on both side edges of each rail groove 221 with the through-holes 222 put therebetween. The shaft cylinder 21 has, as shown in FIG. 2, through-groove shaped suction windows 211, 212, and 213 formed in correspondence with each row of the holding pockets 231 at positions slightly offset on the downstream sides from a tablet feed point, an image pickup point, and a defective tablet ejection point, respectively. A compressed air jetting nozzle 214 and a compressed air jetting space 215 are formed in the shaft cylinder 21 at the defective tablet ejection point and the lowest tablet election point, respectively. Compressed air is supplied from compressed air supply pipes 216 and 217 to the compressed air jetting nozzle 214 and the compressed air jetting space 215, respectively.

The side surface inspecting drum 2 receives flat-shaped tablets "t" fed from the aligning-and-feeding device 13 of the tablet feed unit A in upright states in the holding pockets 231 of the outer cylinder 23, carries the tablets "t" while making them roll on the outer peripheral surface of the inner cylinder 22 by intermittent rotation of the outer cylinder 23, and ejects the tablets "t" from the holding pockets 231 at the lowest tablet ejection point. In the course of the carrying operation, the tablets "t" are photographed at the image pickup point as follows: namely, in the interval during which the outer cylinder 23 is intermittently stopped, the side surface image pickup device 3 photographs each tablet "t" which rotates on its axis in the holding pocket 231 by the continuously rotating inner cylinder 22, to pick up the image of the all-round side surface of the tablet 't".

Figure 4:
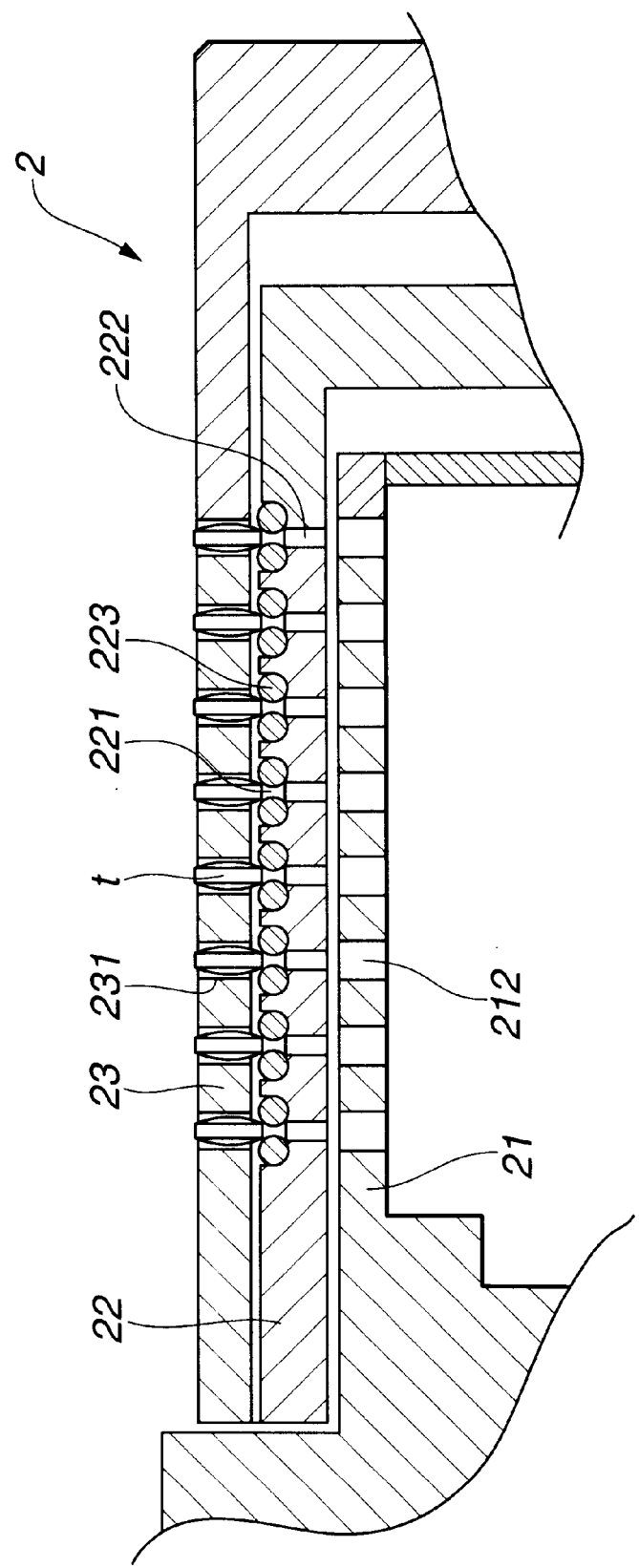
FIG. 4 is a partial enlarged sectional view showing a state in which tablets are held on the side surface inspecting drum.
Figure 5:
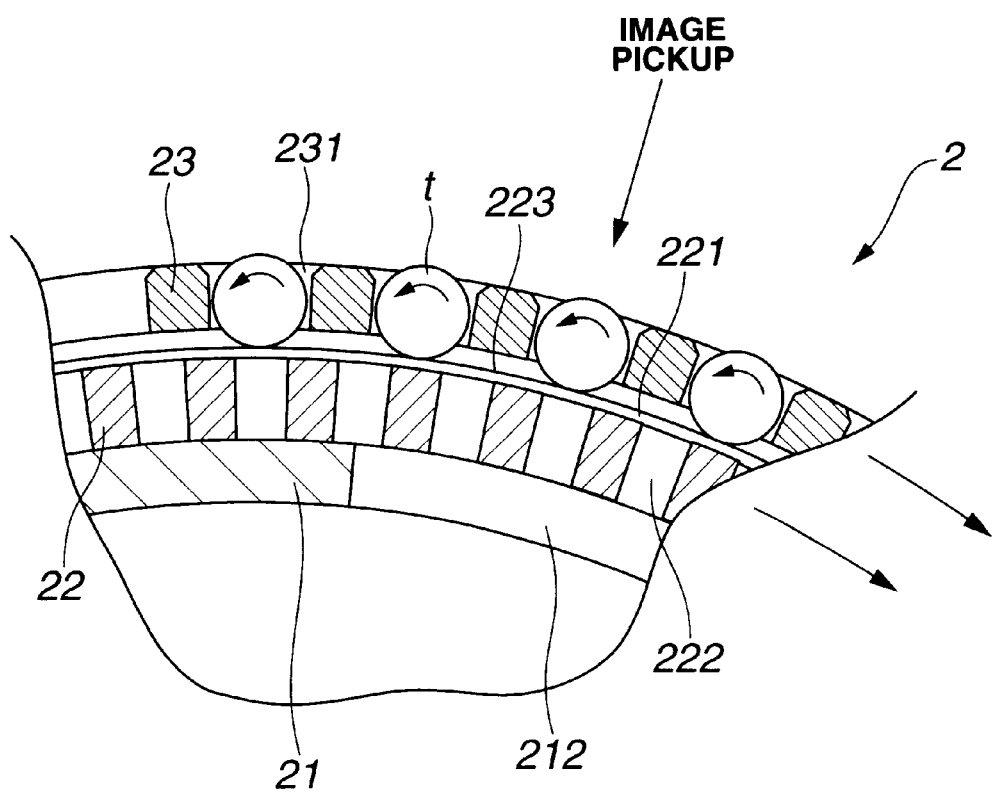
FIG. 5 is a partial enlarged sectional view showing another state in which tablets are held on the side surface inspecting drum.

In this carrying operation, as shown in FIGS. 4 and 5, the tablets "t" carried while being held in the holding pockets 231 of the outer cylinder 23 roll on the pair of rubber rings 223 along each rail groove 221 of the inner cylinder 22. By the way, the inside of the shaft cylinder 21 is usually sucked to be kept in a reduced pressure state, so that at the portions at which the suction windows 211, 212, and 213 are formed, the inside of each rail groove 221 of the inner cylinder 22 is sucked through the suction windows 211, 212, and 213 and the through-holes 222 of the inner cylinder 22. With the aid of this suction force, at the tablet feed point, the tablets "t" are certainly moved from the aligning-and-feeding device 13 of the tablet feed unit A into the holding pockets 231; at the image pickup point, during photographing, the tablets "t" stably rotate on their axes in a state being attracted on the outer peripheral surface of the inner cylinder 22; and on the downstream side from the defective tablet ejection point, the tablets "t" are certainly prevented from being fallen from the holding pockets 231. Additionally, as shown in FIG. 1, a falling preventive guide 34 is disposed along the outer peripheral surface of the side surface inspecting drum 2 at a position between the defective tablet ejection point and the lowest tablet ejection point for preventing the tablets "t" from being fallen from the holding pockets 231.

At the lowest tablet ejection point of the side surface inspecting drum 2, compressed air is usually supplied from the compressed air supply pipe 217 to the compressed air jetting space 215. The compressed air is jetted from each rail groove 221 of the inner cylinder 22 into the holding pockets 231 of the outer cylinder 23 through the through-holes 224 of the inner cylinder 22. With the aid of the compressed air thus jetted, all the tablets "t" carried to the tablet ejection point are certainly ejected from the holding pockets 231.

At the defective tablet ejection point, compressed air is supplied from the compressed air supply pipe 216 to the compressed air jetting nozzle 214 as needed. The compressed air is jetted from each rail groove 221 of the inner cylinder 22 into the holding pockets 231 of the outer cylinder 23 through the through-holes 222 of the inner cylinder 22. With the aid of the compressed air thus jetted, defective tablets each having an appearance defect on the side surface are selectively ejected from the holding pockets 231, and are recovered in the defective recovery can 33 disposed outside the side surface inspecting drum 2 at a position corresponding to the defective tablet ejection point (see FIG. 1).

While not shown, the tablet appearance inspecting apparatus of the present invention is provided with a side surface defective decision unit for processing the image of the side surface of each tablet picked up by the side surface image pickup device 3 and detecting the presence or absence of the appearance defect on the side surface of the tablet. The compressed air is supplied from the compressed air supply pipe 216 to the compressed air jetting nozzle 214 on the basis of the decision result obtained by the side surface defective decision unit, and only the defective tablet is selectively ejected from the holding pocket 231 and is recovered in the defective recovery can 33 by the compressed air.

Next, the front and back surface inspecting unit C will be described. The front and back surface inspecting unit C is, as described above, composed of the front and back surface inspecting apparatus according to the embodiment of the present invention. As shown in FIG. 1, the front and back surface inspecting unit C includes a front surface inspecting drum 4 and a back surface inspecting drum 5 each of which carries flat-shaped tablets while holding the tablets in falling-down states with the thickness direction of the tablets directed in the vertical direction; a front surface image pickup device 7 and a back surface image pickup device 8 which photograph the tablets held on the outer peripheral surface of the front surface inspecting drum 4 and the tablets held on the outer peripheral surface of the back surface inspecting drum 5, thereby picking up images of the front surfaces and back surfaces of the tablets, respectively; and a tablet feed unit 6 for feeding tablets to be inspected to the outer peripheral surface of the front surface inspecting drum 4. Additionally, in FIG. 1, reference numeral 71 and 81 designate cameras, and 72 and 82 are illuminating devices.

Figure 6:
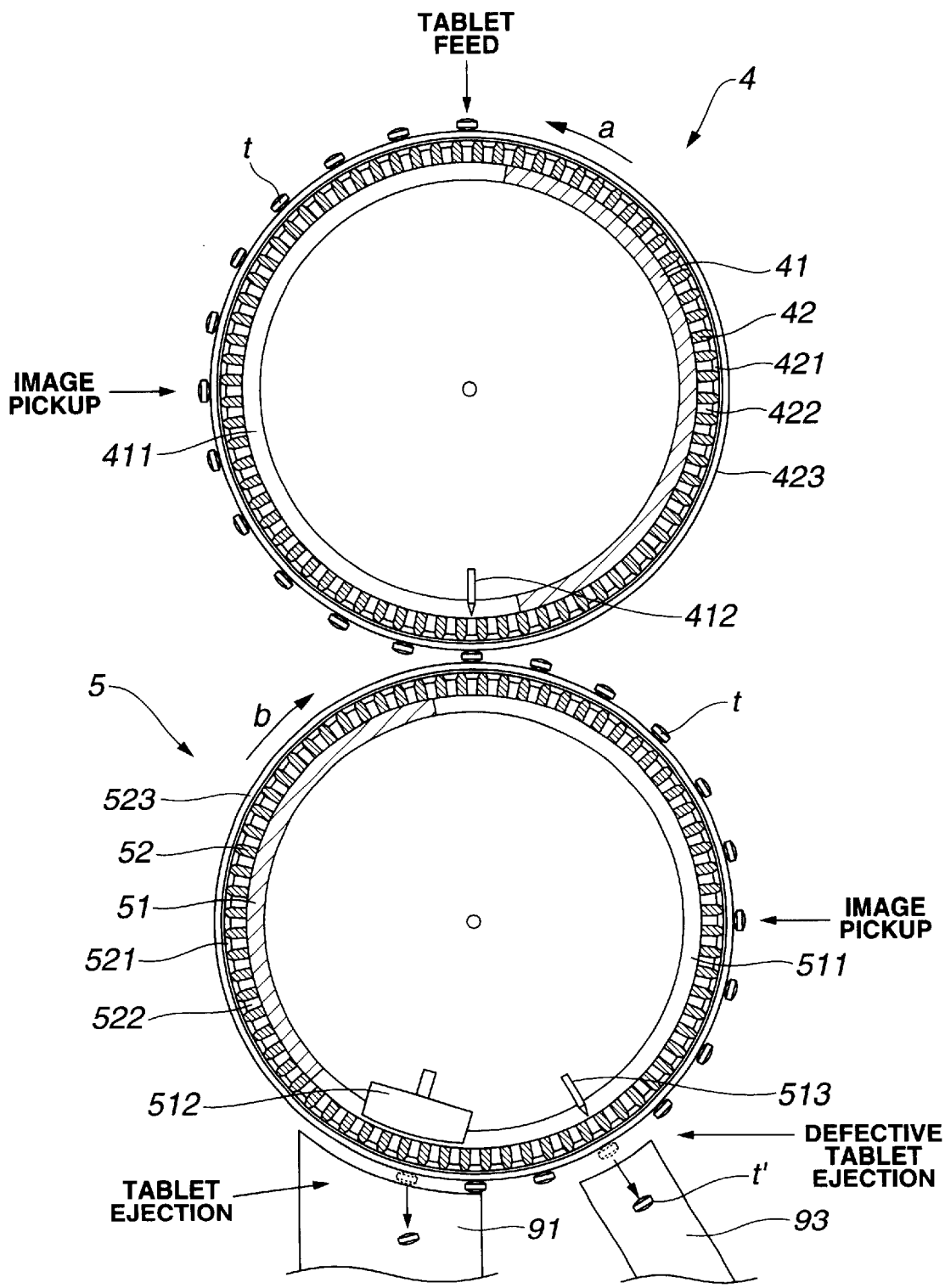
FIG. 6 is a schematic sectional view showing a front surface inspecting drum and a back surface inspecting drum of the front and back surface inspecting apparatus.

The front surface inspecting drum 4 and the back surface inspecting drum 5 include, as shown in FIG. 6, inner cylinders 41 and 51, and outer cylinders 42 and 52 rotatably disposed on the outer peripheral sides of the inner cylinders 41 and 51, respectively. The outer cylinder 42 of the front surface inspecting drum 4 continuously rotates counter-clockwise (in the direction "a") in FIG. 6 along the outer periphery of the inner cylinder 41 at a specific speed. The outer cylinder 52 of the back surface inspecting drum 5 continuously rotates clockwise (in the direction "b") in FIG. 6 along the outer periphery of the inner cylinder 51 at a specific speed.

Figure 7:
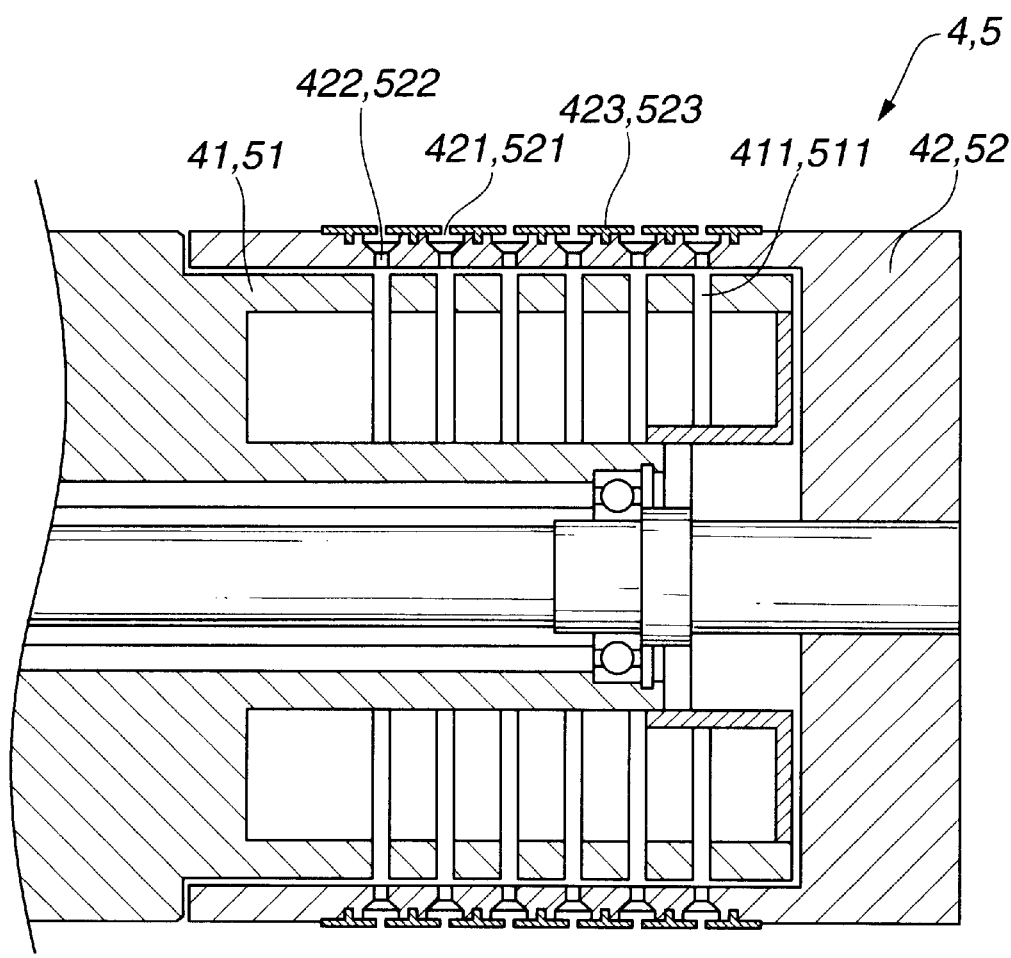
FIG. 7 is a sectional view showing the front surface inspecting drum and the back surface inspecting drum.
Figure 8:
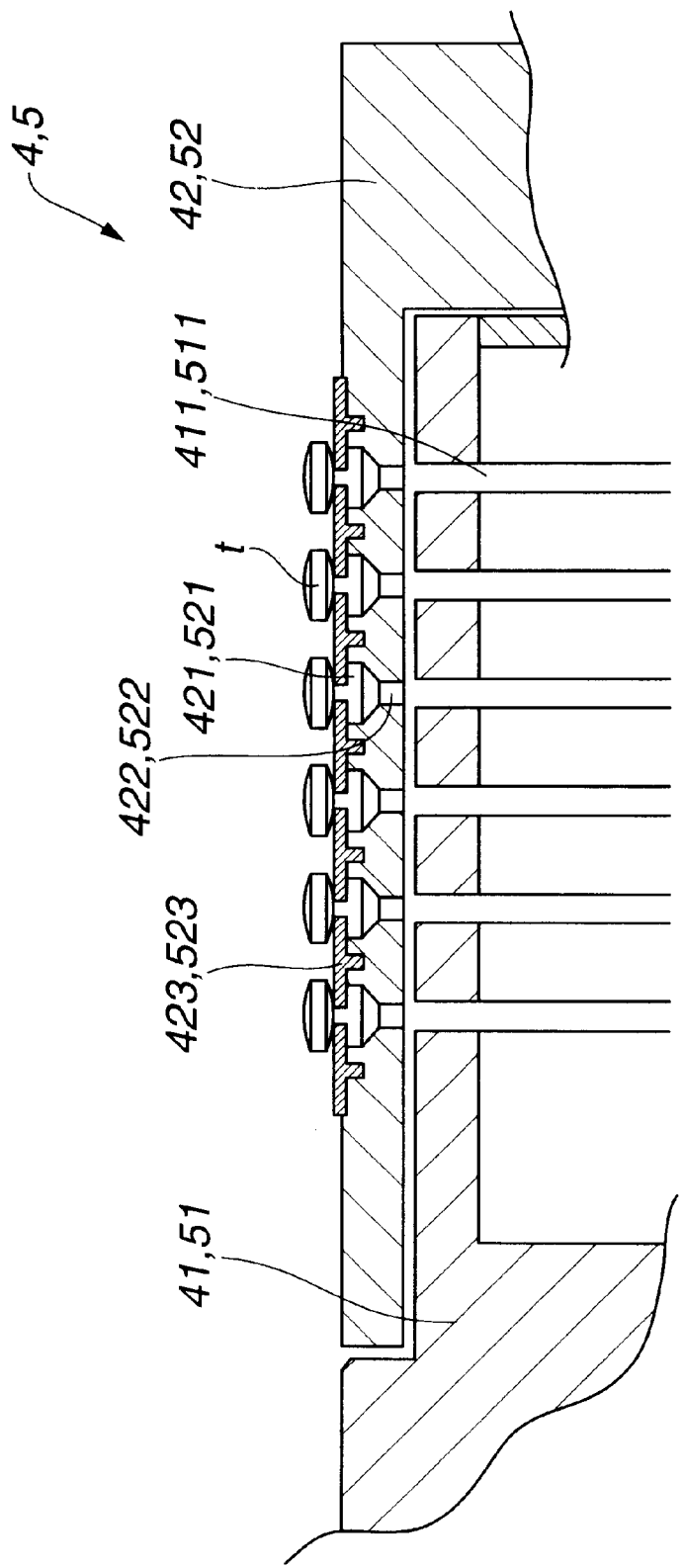
FIG. 8 is a partial enlarged sectional view showing a state in which tablets are held on the front surface inspecting drum and the back surface inspecting drum.

The inner cylinder 41 has a circumferential through-groove 411 having a length of about the semi-circumference of the inner cylinder 41 which nearly corresponds to the carrying region of tablets. Similarly, the inner cylinder 51 has a circumferential through-groove 511 having a length of about the semi-circumference of the inner cylinder 51 which nearly corresponds to the carrying region of tablets. As shown in FIGS. 7 and 8, the outer peripheral surface of the outer cylinder 42 has a plurality of (six in the figure) of suction grooves 421 extending in the circumferential direction, and similarly, the outer peripheral surface of the outer cylinder 52 has a plurality of (six in the figure) of suction grooves 521 extending in the circumferential direction. In each of the suction grooves 421, a number of suction holes 422 are aligned in the circumferential direction, and in each of the suction grooves 521, a number of suction holes 522 are aligned in the circumferential direction. As shown in FIGS. 7 and 8, a pair of rubber rings 423 formed into T-shape in cross-section are mounted on the outer cylinder 42 in such a manner as to extend along both side edges of each suction groove 421 with the suction holes 422 put therebetween, and similarly, a pair of rubber rings 523 are mounted on the outer cylinder 52 in such a manner as to extend along both side edges of each suction groove 521 with the suction holes 522 put therebetween.

Figure 9:
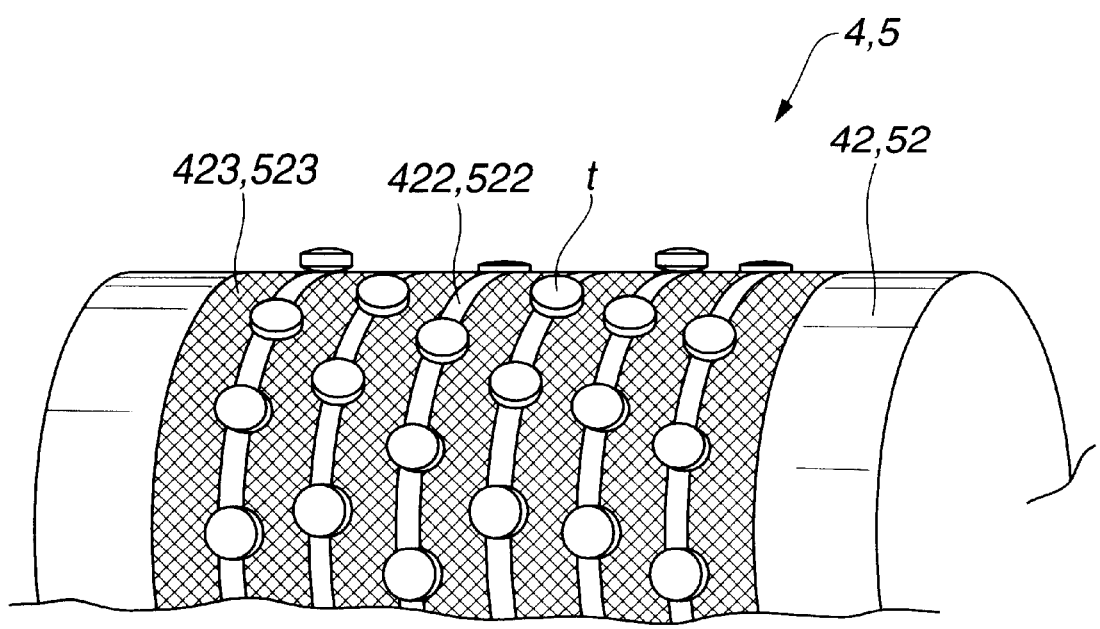
FIG. 9 is a partial perspective view showing another state in which tablets are held on the front surface inspecting drum and the back surface inspecting drum.

The inside of the inner cylinder 41 is usually sucked to be kept in a reduced pressure state, and in the carrying region of tablets, the inside of each suction groove 421 is sucked from the suction holes 422 of the outer cylinder 42 through the through-grooves 411, and similarly, the inside of the inner cylinder 51 is usually sucked to be kept in a reduced pressure state, and in the carrying region of tablets, the inside of each suction groove 521 is sucked from the suction holes 522 of the outer cylinder 52 through the through-grooves 511. With the aid of this suction force, as shown in FIGS. 8 and 9, the tablets "t" are attractively held on the outer peripheral surface of the outer cylinder 42 at positions over the through-groove 411 while lying astride the adjacent rubber rings 423, and similarly the "tablets" are attractively held on the outer peripheral surface of the outer cylinder 52 at positions over the through-groove 511 while lying astride the adjacent rubber rings 523.

The front surface inspecting drum 4 and the back surface inspecting drum 5 are disposed in parallel in the vertical direction with their outer peripheral surfaces made in proximity to each other. The back surface inspecting drum 5 is disposed under the front surface inspecting drum 4. The tablets "t" are fed from the tablet feed unit 6 to the top portion of the front surface inspecting drum 4, being held on the outer peripheral surface of the outer cylinder 42 of the front surface inspecting drum 4, and are carried downwardly by rotation of the outer cylinder 42. In the course of carrying operation, the tablets are photographed by the front surface image pickup device 7 (see FIG. 1). Then, the tablets are delivered from the lowest portion of the front surface inspecting drum 4 to the back surface inspecting drum 5, being held on the outer peripheral surface of the outer cylinder 52 of the back surface inspecting drum 5, and carried downwardly by rotation of the outer cylinder 52. In the course of carrying operation, the tablets are photographed by the back surface image pickup device 8 (see FIG. 1), and are ejected from the lowest portion of the back surface inspecting drum 5 into a non-defective ejection chute 91.

A compressed air jetting nozzle 412 is, as shown in FIG. 6, disposed in the front surface inspecting drum 4 at the lowest portion thereof. The tablets are desirably delivered from the front surface inspecting drum 4 to the back surface inspecting drum 5 by the compressed air jetted from the compressed air jetting nozzle 412.

Figure 10:
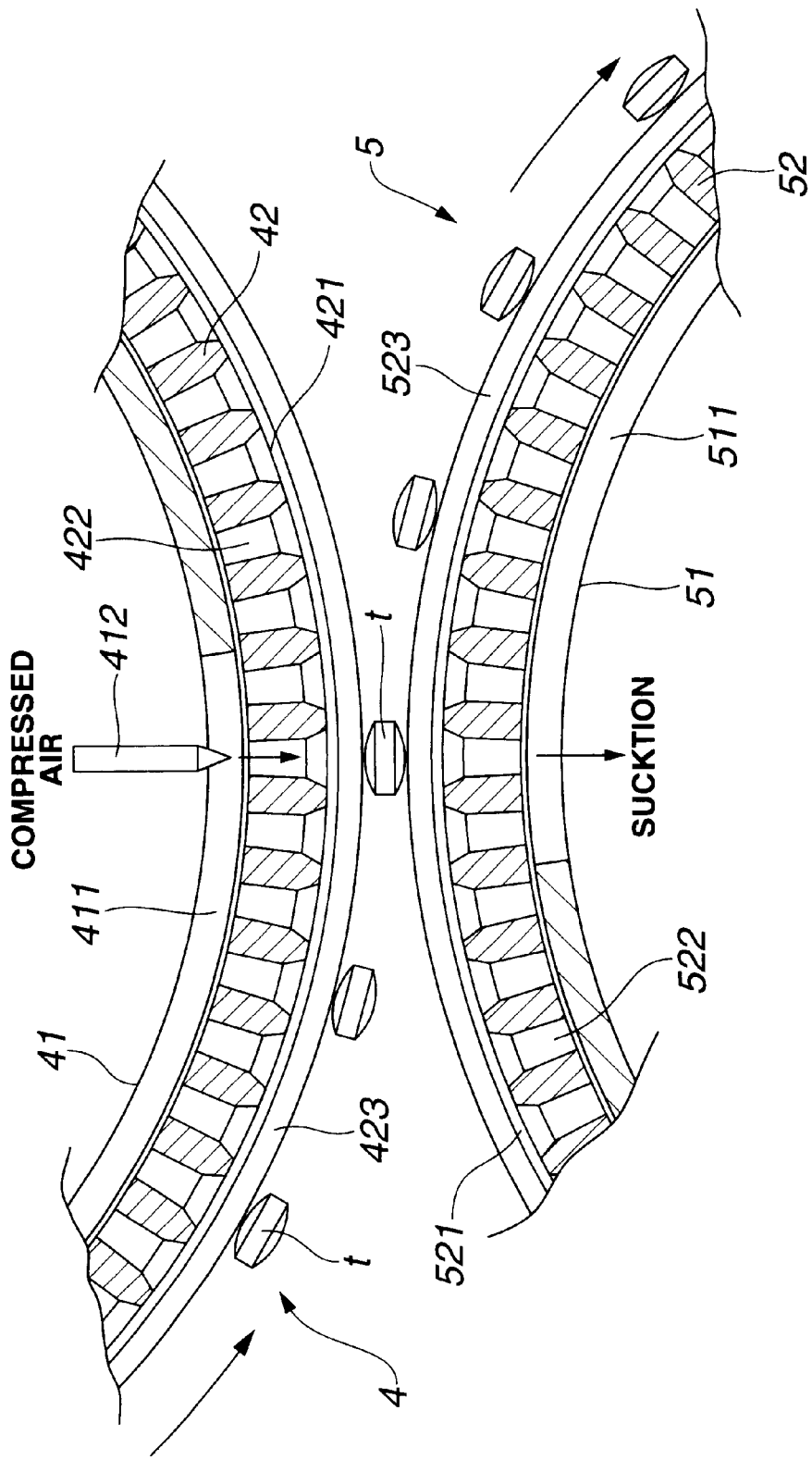
FIG. 10 is a partial enlarged sectional view showing a state in which tablets are delivered from the front surface inspecting drum to the back surface inspecting drum.

To be more specific, as shown in FIG. 10, the delivery of each tablet "t" from the front surface inspecting drum 4 to the back surface inspecting drum 5 is made as follows. The tablet "t" is pinched once between the rubber rings 423 of the front surface inspecting drum 4 and the rubber rings 523 of the back surface inspecting drum 5. At this time, compressed air jetted from the compressed air jetting nozzle 412 disposed inside the front surface inspecting drum 4 is jetted from the suction groove 421 of the outer cylinder 42 through the through-groove 411 of the inner cylinder 41 and the suction hole 422 of the outer cylinder 42. The tablet "t" is released from the outer peripheral surface of the front surface inspecting drum 4 by the compressed air thus jetted, and is simultaneously sucked from the inner cylinder 51 side of the back surface inspecting drum 5, to be attracted on the outer peripheral surface of the back surface inspecting drum 5. In this way, the tablet "t" is smoothly delivered from the front surface inspecting drum 4 to the back surface inspecting drum 5.

A compressed air jetting box 512 is, as shown in FIG. 6, disposed in the back surface inspecting drum 5 at the lowest portion thereof. Compressed air is usually jetted from the compressed air jetting box 512, and such compressed air is jetted from each suction groove 521 of the outer cylinder 52 onto the outer peripheral surface of the back surface inspecting drum 5 through each through-groove 511 of the inner cylinder 51 and the suction holes 522 of the outer cylinder 52, so that the tablets "t" held on the outer peripheral surface of the back surface inspecting drum 5 are desirably ejected into the non-defective ejection chute 91.

A compressed air jetting nozzle 513 for ejecting defectives is, as shown in FIG. 6, disposed in the back surface inspecting drum 5 at a position offset slightly on the downstream side from the tablet ejection point of the back surface inspecting drum 5. Compressed air is jetted from the compressed air jetting nozzle 513 as needed, and such compressed air is jetted from each suction groove 521 of the outer cylinder 52 through each through-groove 511 of the inner cylinder 51 and the suction holes 522 of the outer cylinder 52. A defective tablet "t" having an appearance defect on the front surface and/or back surface is selectively excluded from the outer peripheral surface of the back surface inspecting drum 5 and is ejected in a defective tablet ejection chute 93.

While not shown, the tablet appearance inspecting apparatus of the present invention includes a front and back surface defective decision unit for processing images of front and back surfaces of each tablet picked up by the front surface image pickup device 7 and the back surface image pickup device 8 and detecting the presence or absence of an appearance defect on the front surface and/or back surface of the tablet. Compressed air is jetted from the compressed air jetting nozzle 513 on the basis of the decision result obtained by the front and back surface defective decision unit, and only the defective tablet "t'" is selectively excluded from the peripheral surface of the back surface inspecting drum 5 and is ejected in the defective ejection chute 93 by the compressed air. Additionally, the fact that the defective tablet "t'" is carried to the position of the compressed air jetting nozzle 513 can be easily acknowledged on the basis of a time elapsed since the image of the front or back surface of the tablet "t'" is picked up by the front surface image pickup device 7 or the back surface image pickup device 8.

In FIG. 9, reference numeral 95 designates cleaning devices for cleaning the outer peripheral surfaces of the front surface inspecting drum 4 and the back surface inspecting drum 5.

The tablet feed unit 6 for feeding tablets "t" to be inspected on the outer peripheral surface of the front surface inspecting drum 4 will be described below. The tablet feed unit 6 includes a tablet storing portion 61 for storing once the tablets ejected from the side surface inspecting drum 2 of the side surface inspecting unit B; a vibration plate 62 for carrying the tablets in the tablet storing portion 61 onto the front surface inspecting drum 4; and a tablet feed roller 63 for moving the tablets from the leading end of the vibration plate 62 onto the front surface inspecting drum 4.

Figure 11:
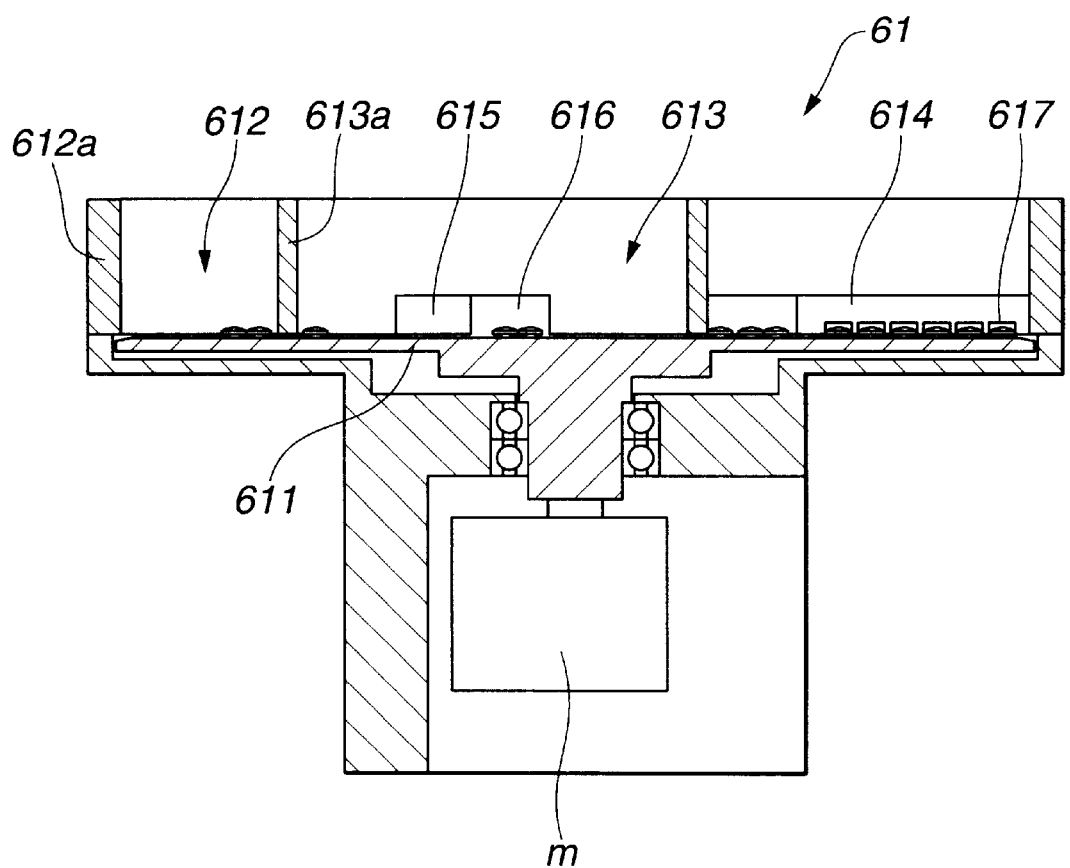
FIG. 11 is a schematic sectional view showing a tablet storing portion of the front and back surface inspecting apparatus.
Figure 12:
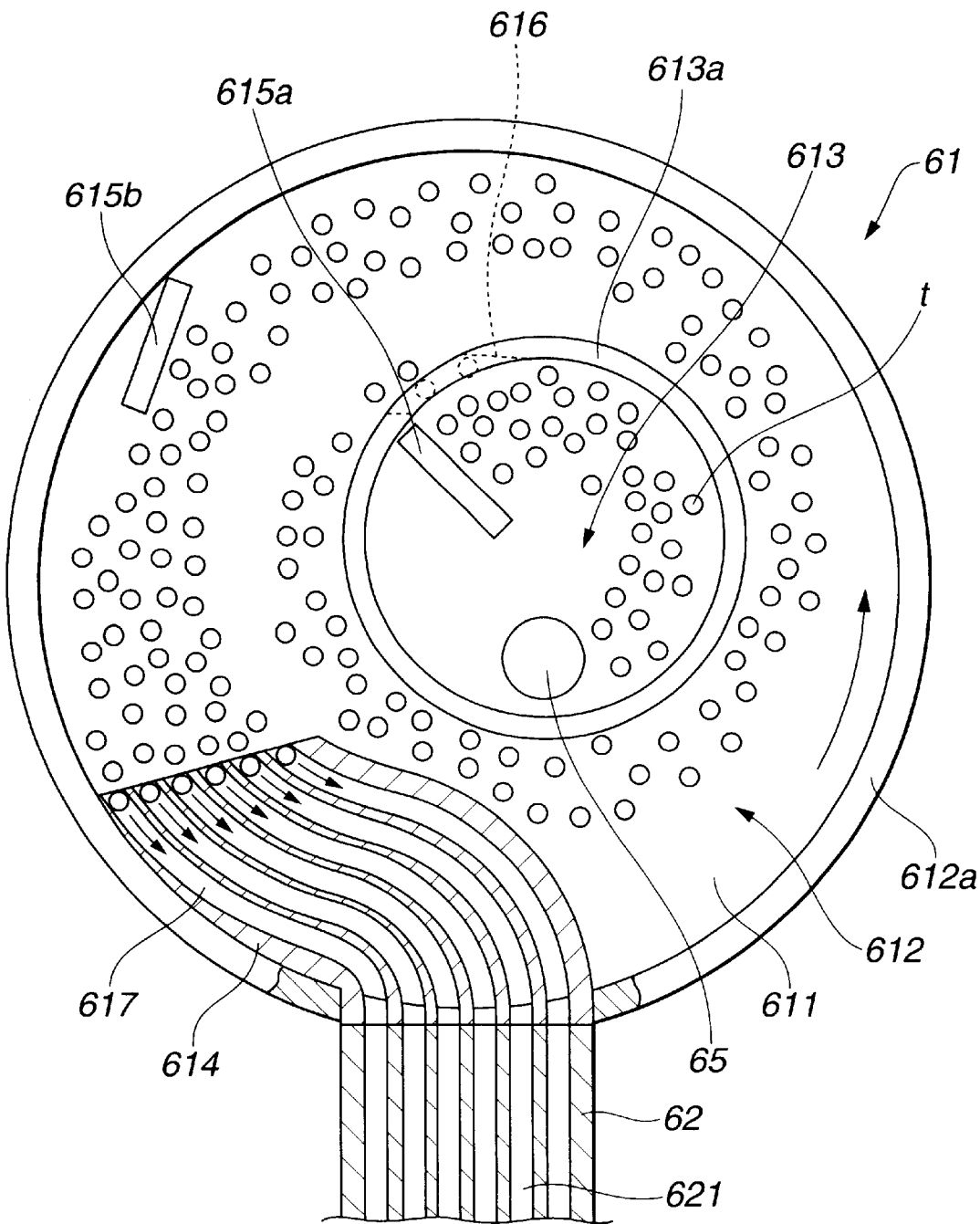
FIG. 12 is a schematic plan view showing the tablet storing portion.

The tablet storing portion 61 includes, as shown in FIGS. 11 and 12, a turn table 611 rotated at a specific speed by a motor "m"; an outer chamber 612 formed on the turn table 611 by a ring-shaped peripheral wall 612a disposed concentrically with the rotational center of the turn table 611; an inner chamber 613 formed on the turn table 611 by a ring-shaped peripheral wall 613a which has a diameter smaller than the diameter of the outer chamber 612 and which is disposed inside the outer chamber 612 eccentrically from the rotational center of the turn table 611; and a communication member 614 disposed on the turn table 611 while being located inside the outer chamber 612.

The peripheral wall 613a, which forms the inner chamber 613, has at its portion a communication window 616 communicated to the outer chamber 612. A barrier wall 615a is provided in the inner chamber 613 at a position near the communication window 616. The tablets "t" in the inner chamber 613, which move circularly by rotation of the turn table 611, are shifted to the communication window 616 side by the barrier wall 615a, and move to the outer chamber 612 through the communication window 616. A barrier wall 615b similar to the barrier wall 615a is provided in the outer chamber 612 at a position near the communication member 614. The tablets, which have been shifted to the peripheral edge portion of the outer chamber 612 by the centrifugal force, are returned to the inner side of the outer chamber 612 by the barrier wall 615b, to be thus smoothly guided to the communication member 614.

As shown in FIG. 12, the communication member 614 is formed into an approximately plate shape arcuately curved along the peripheral edge portion of the outer chamber 612. The communication member 614 extending along the peripheral edge of the outer chamber 612 is disposed in such a manner as to be nearly in contact with a portion, located in the outer chamber 612, of the turn table 611. One end of the communication member 614 is opposed to the rotational direction of the turn table 611, and the other end thereof passes through the peripheral wall 61a of the outer chamber 612 and is connected to the vibration plate 62. The communication member 614 has a plurality of (six in the figure) communication passages 617 with the lower surfaces thereof opened. Each of the communication passages 617 has a width and a height set to allow the tablet "t" in the falling-down state to pass therethrough. The opened lower surface of the communication passage 617 is closed with the rotating tun table 611. One end of the communication passage 617, which is located in the outer chamber 612, is opened on the turn table 611 while being opposed to the rotational direction of the turn table 611, and the other end thereof is connected to a tablet feed passage 621 of the vibration plate 62.

Figure 13:
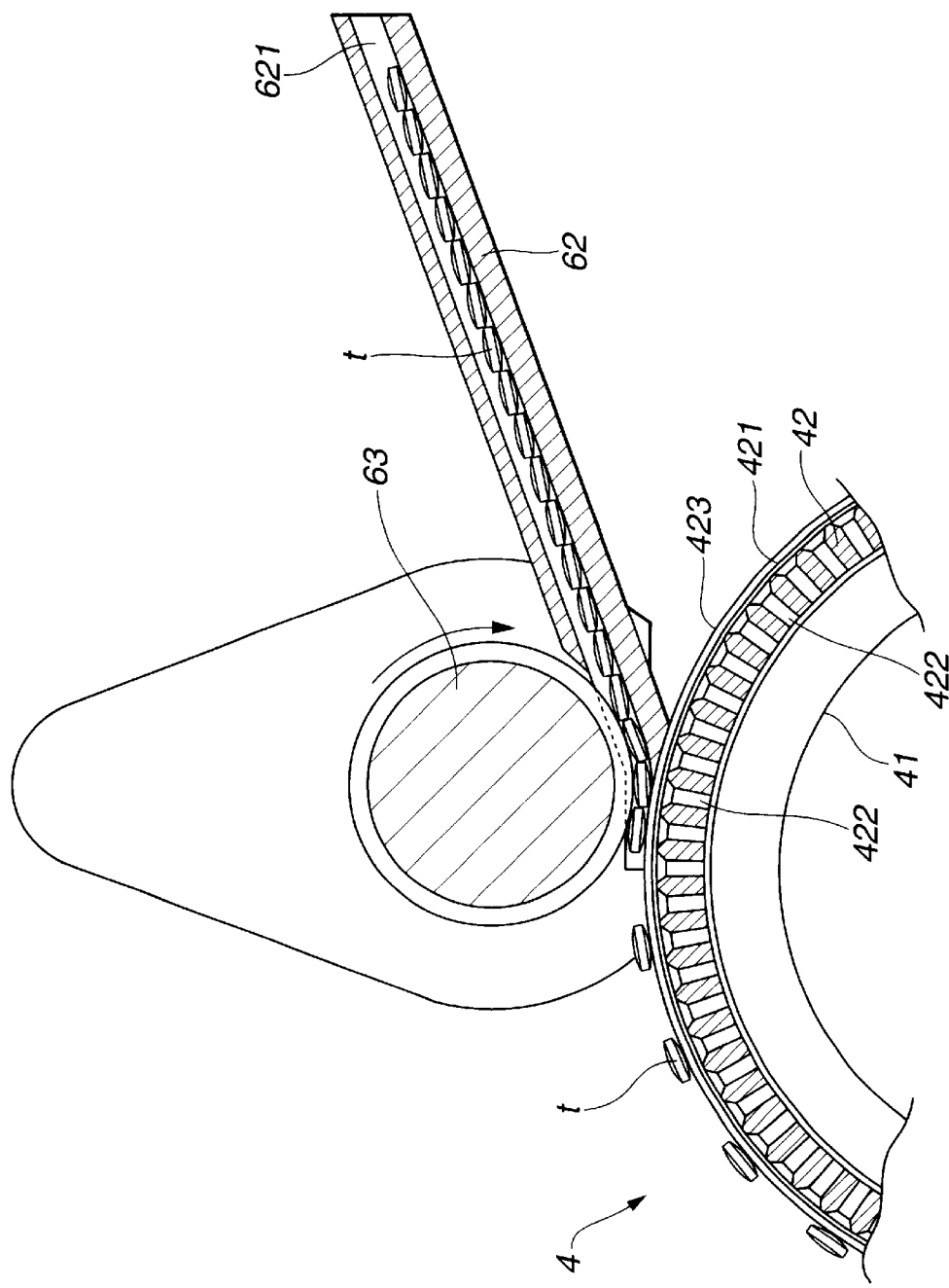
FIG. 13 is a schematic view of the front and back surface inspecting apparatus, showing a state in which tablets are fed from a vibration plate to the front surface inspecting drum.
Figure 14:
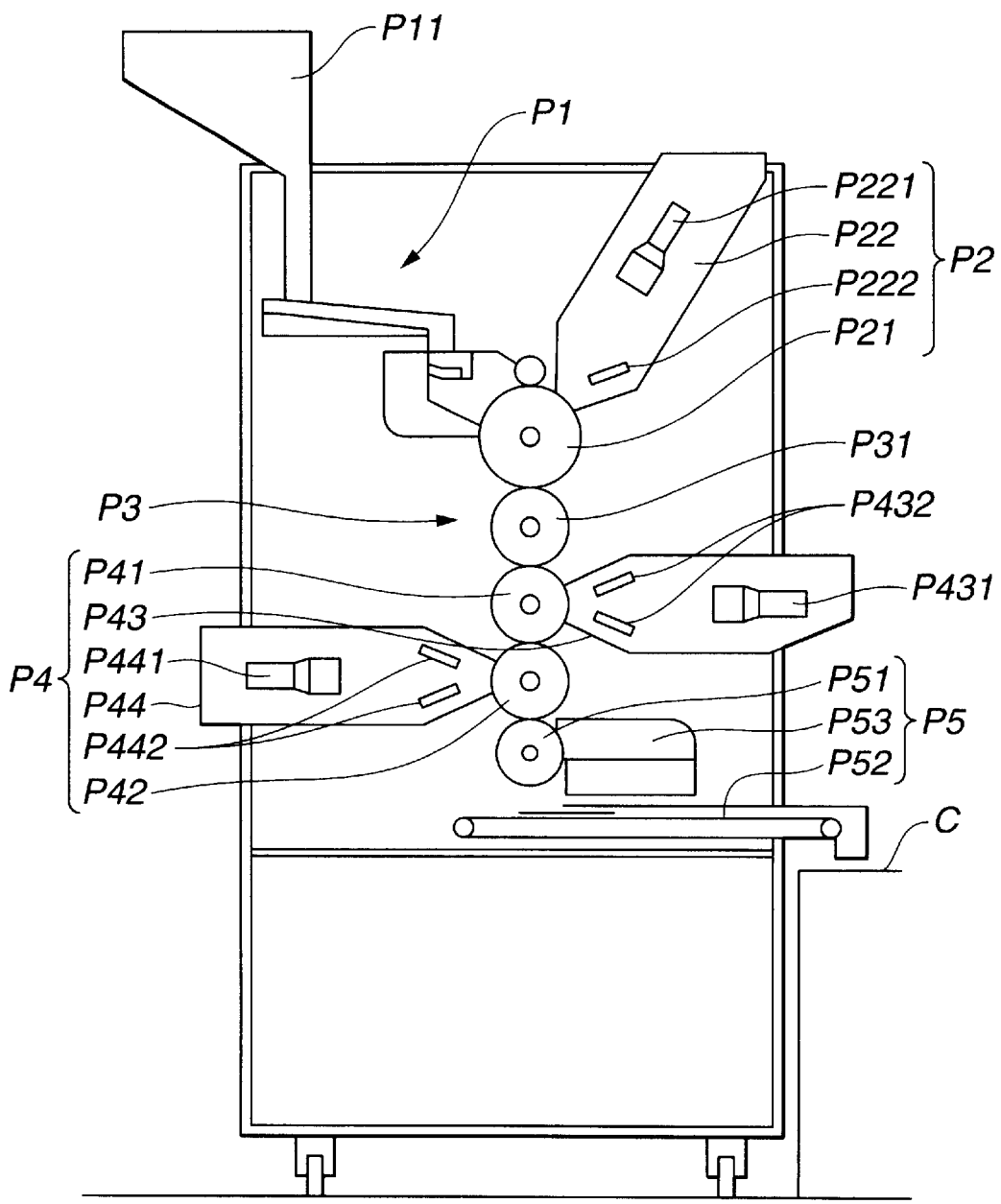
FIG. 14 is a schematic view showing a prior art tablet appearance inspecting apparatus.
Figure 15:
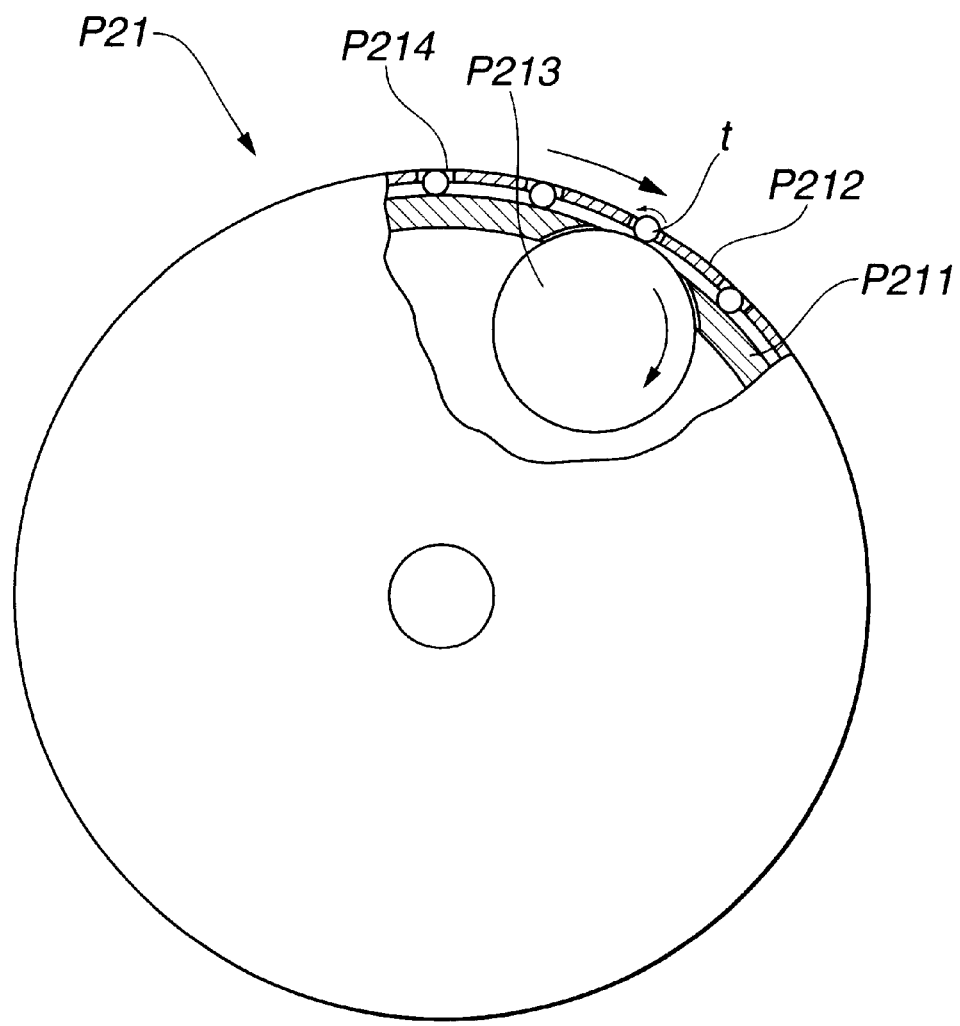
FIG. 15 is a schematic view, with parts partially cutaway, showing a side surface inspecting drum of the prior art tablet appearance inspecting apparatus.
Figure 16:
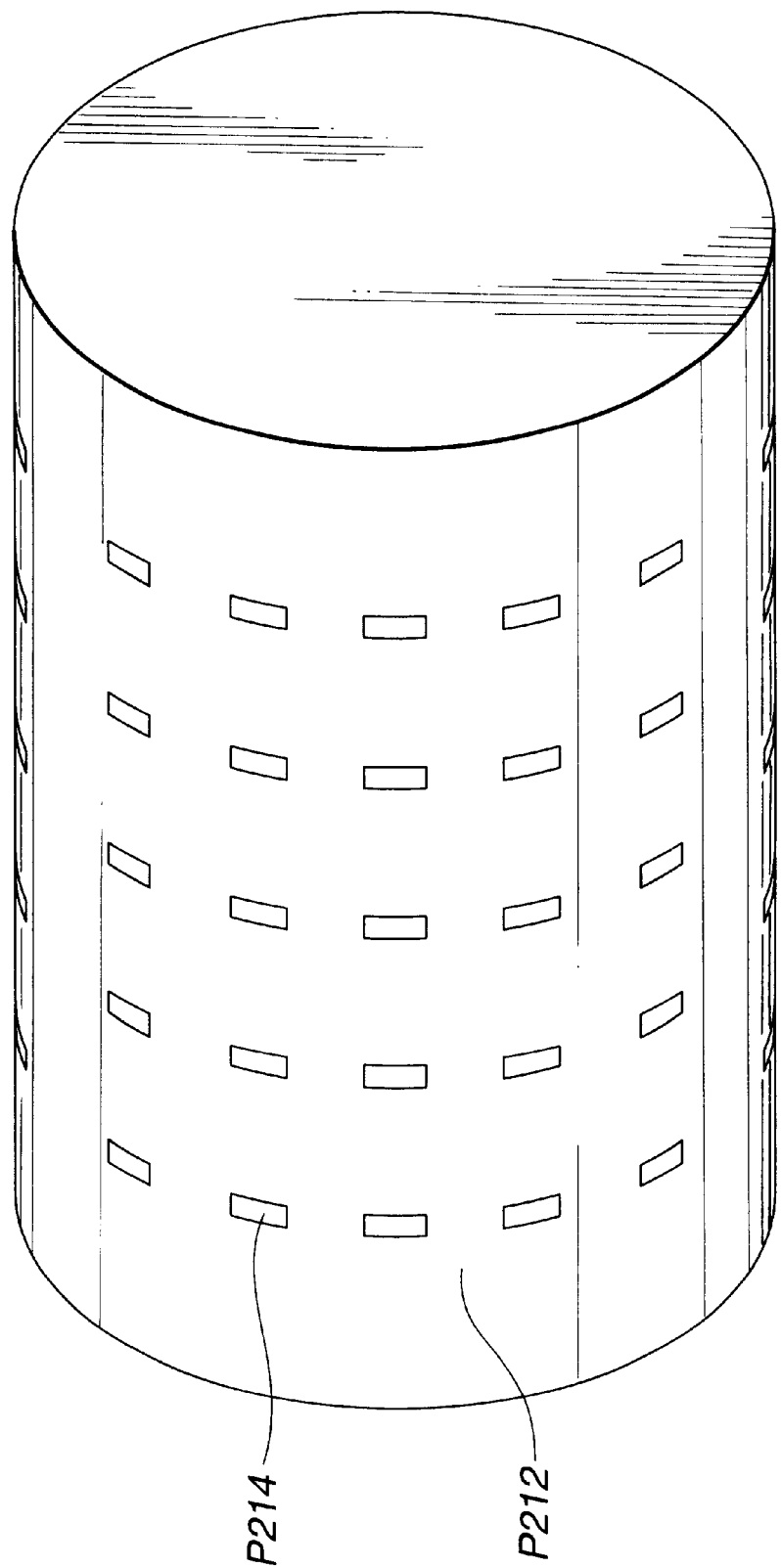
FIG. 16 is a perspective view showing an outer cylinder of the side surface inspecting drum of the prior art tablet appearance inspecting apparatus.
Figure 17:
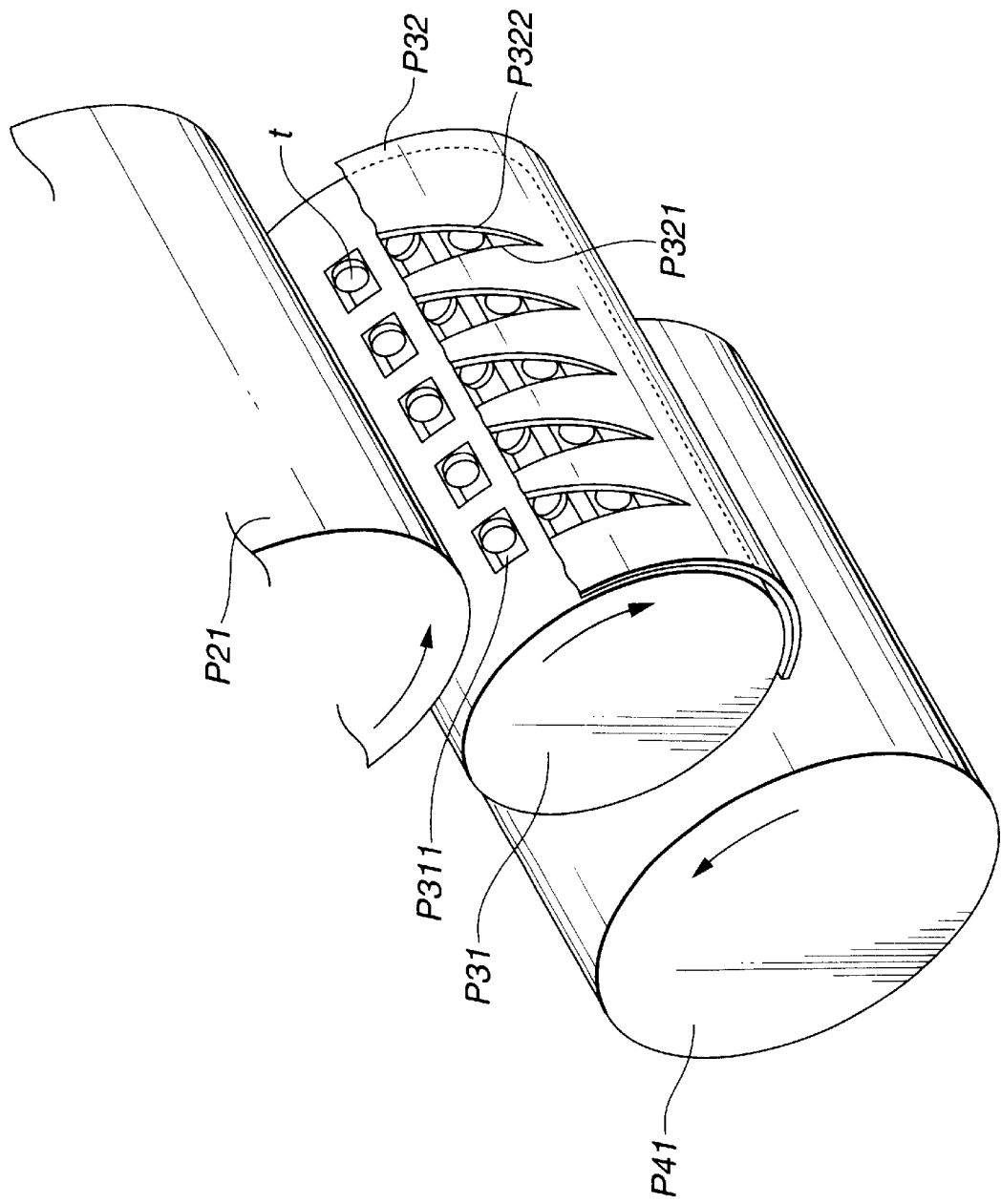
FIG. 17 is a schematic perspective view of the prior art tablet appearance inspecting apparatus, illustrating the operation to change the postures of tablets from upright postures to falling-down postures.

As shown in FIG. 13, the vibration plate 62 is disposed while being tilted downwardly toward the front surface inspecting drum 4 by a specific angle in a state in which one end thereof is positioned near the outer peripheral surface of the front surface inspecting drum 4 and the other end thereof is connected to the above communication member 614. The vibration plate 62 has a plurality of (six in this embodiment) tablet feed passages 621 each having a size to allow the tablet "t" in the falling-down state to pass therethrough. In addition, the upper surface of the one end portion, disposed near the front surface inspecting drum 4, of the tablet feed passage 621 is partially opened.

The vibration plate 62 is finely vibrated by a vibration generator (see FIG. 1). With the aid of the vibration, the tablets "t" introduced from the communication passages 617 of the communication member 614 into the tablet feed passages 621 are continuously moved to the one end portions, being in proximity to the outer peripheral surface of the front surface inspecting drum 4, of the tablet feed passages 621.

The tablet feed roller 63 is configured as an elastic roller made from silicone rubber. As shown in FIG. 13, the outer peripheral portion of the tablet feed roller 63 partially enters the tablet feed passages 621 through the above-described opened portion formed at the one end portion of the vibration plate 62. The tablet feed roller 63 is rotated at a suitable constant speed for moving the tablets "t" from the one end portion of the vibration plate 62 onto the front surface inspecting drum 4 at a suitable speed.

The tablet feed unit 6 including the above-described tablet storing portion 61, vibration plate 62, and tablet feed roller 63 are used to continuously feed the tablets ejected from the side surface inspecting drum 2 of the side surface inspecting unit B onto the outer peripheral surface of the front surface inspecting drum 4 in falling-down states.

To be more specific, the tablets "t" ejected from the side surface inspecting drum 2 of the side surface inspecting unit B are continuously fed in the inner chamber 613 of the tablet storing portion 61 through the communication chute 65 (see FIG. 1). The tablets "t" fed in the inner chamber 613 are circularly moved by the rotation of the turn table 611 to be shifted outwardly by the centrifugal force, and are sequentially moved into the outer chamber 612 through the communication window 616. The tablets "t" moved in the outer chamber 612 are rotated while being shifted outwardly by the centrifugal force due to the rotation of the turn table 611, to enter the communication passages 617 of the communication member 614. The tablets "t" are then continuously introduced into the tablet feed passages 621 of the vibration plate 62 through the communication passages 617, being sequentially moved from the one end portion of the vibration plate 62 onto the outer peripheral surface of the front surface inspecting drum 4 by the tablet feed roller 63, and are continuously fed to the front surface inspecting drum 4 at a specific speed.

The operation of the tablet appearance inspecting apparatus in this embodiment will be described below.

The tablet appearance inspecting apparatus in this embodiment is operated to inspect side surfaces of tablets fed from the tablet feed unit A by the side surface inspecting unit B and selectively exclude defective tablets each having an appearance defect on the side surface of the tablet; feed all of the tablets with no defect on the side surfaces from the side surface inspecting drum 2 of the side surface inspecting unit B into the tablet storing portion 61 of the front and back surface inspecting unit C; inspect front and back surfaces of the tablets by the front and back surface inspecting unit C and selectively exclude defective tablets each having an appearance defect on the front or back surface of the tablet; and recover non-defective tablets each having no appearance defect on the side surface and the front and back surfaces of the tablet from the front and back surface inspecting drum 5 of the front and back surface inspecting unit C.

First, tablets fed at random from the hopper 11 of the tablet feed unit A are charged in the alignment-and-feeding device 13 at a specific speed by the vibration feeder 12, and the tablets are charged, in the upright states, from the alignment-and-feeding device 13 into the holding pockets 231 formed in the outer cylinder 23 of the side surface inspecting drum 2 of the side surface inspecting unit B.

The tablets "t" held in the holding pockets 231 formed in the outer cylinder 23 of the side surface inspecting drum 2 are, as shown in FIGS. 4 and 5, carried downwardly while being kept in the upright states by the intermittent rotation of the outer cylinder 23. At this time, the tablets "t" roll on the rubber rings 223 mounted on the outer peripheral surface of the continuously rotating inner cylinder 22. When each of the tablets "t" is carried to the image pickup point at which the tablets are to be photographed by the side surface image pickup device 3 and the rotation of the outer cylinder 23 is intermittently stopped, the tablet "t" rolls on the outer peripheral surface (on the rubber rings 223) of the continuously rotating inner cylinder 22 while being held and stopped in the holding pocket 231, that is, rotates on its axis. In such a state, the side surface image pickup device 3 photographs the tablet "t", to pick up the image of the all-round side surface of the tablet "t".

The image of the side surface of the tablet "t" is processed by the side surface detective decision unit, to decide the presence or absence of an appearance defect on the side surface of the tablet "t". If it is decided that the side surface of the table "t" has an appearance defect, the defective tablet is ejected as follows: namely, when the defective tablet is carried to the defective tablet ejection point shown in FIG. 2 by the intermittent rotation of the outer cylinder 23, the defective tablet is ejected from the holding pocket 231 of the outer cylinder 23 by compressed air jetted from the compressed air jetting nozzle 214 of the inner cylinder 22, to be recovered in the defective recovery can 33.

If it is decided that the side surface of the tablet "t" has no appearance defect, such a non-defective tablet is further carried downwardly by the intermittent rotation of the outer cylinder 23 and is ejected, at the lowest portion of the side surface inspecting drum 2, from the holding pocket 231 of the outer cylinder 23 by compressed air jetted from the compressed air jetting space 215 of the inner cylinder 22. In this way, the non-defective tablets "t" are continuously charged in the tablet storing portion 61 of the tablet feed unit 6 of the front and back surface inspecting unit C through the communication chute 65.

The tablets "t", each having no appearance defect on the side surface, charged in the tablet storing portion 61 are, as shown in FIG. 12, stored on a portion, located in the inner chamber 613, of the turn table 611 through the communication chute 65. The tablets "t" are circularly moved in the falling-down states by the rotation of the turn table 611 to be shifted outwardly in the inner chamber 613 by the centrifugal force, and are sequentially moved to the outer chamber 612 through the communication window 616 provided in the peripheral wall 613a of the inner chamber 613. The tablets "t" moved in the outer chamber 612 are circularly moved in the falling-down states by the rotation of the turn table 611, being pushed outwardly by the centrifugal force and the outer peripheral surface of the peripheral wall 613a , and are further moved outwardly in the outer chamber 612. The tablets "t" thus moved outwardly enter, in the falling-down states, the communication passages 617 of the communication member 614 disposed along the peripheral edge portion of the outer chamber 612, to be introduced in the tablet feed passages 621 of the vibration plate 62 through the communication passages 617.

The tablets "t" introduced in the tablet feed passages 621 of the vibration plate 62 are, as shown in FIG. 13, sequentially moved, while being kept in the falling-down states, to the one end portion of the vibration plate 62 disposed in proximity to the outer peripheral surface of the front surface inspecting drum 4 by fine vibration of the vibration plate 62. The tablets "t" are fed, one by one, from the one end portion of the vibration plate 62 to the outer peripheral surface of the front surface inspecting drum 4 at a specific speed by the tablet feed roller 63 rotating at a specific speed.

The tablets "t" fed on the front surface inspecting drum 4 are, as shown in FIGS. 8 and 9, are attractively held in the falling-down states on the rubber rings 423 mounted on the outer periphery of the outer cylinder 42, and are carried downwardly by the continuous rotation of the outer cylinder 42. Here, the tablets "t" in each row are fed from the vibration plate 62 to the front surface inspecting drum 4 at constant intervals corresponding to the rotational speed of the tablet feed roller 63; however, the feeding timing of the tablets "t" in one row is different from the feeding timing of the tablets "t" in another row, and accordingly, as shown in FIG. 9, the tablets "t" held on the front surface inspecting drum 4 are carried at constant intervals in each tablet row but are carried at random between respective tablet rows.

Each tablet "t" carried while being attractively held on the outer peripheral surface of the outer cylinder 42 of the front surface inspecting drum 4 is photographed by the front surface image pickup device 7 at the image pickup point shown in FIG. 6, and the image of the front surface of the tablet "t" is picked up by the front surface image pickup device 7. The front and back surface defective decision unit processes the image of the front surface of the tablet "t", to decide the presence or absence of an appearance defect. The decision result is stored in the front and back surface defective decision unit. After the above photographing, the tablets 't" are further carried downwardly, and are delivered from the lowest portion of the front surface inspecting drum 4 to the back surface inspecting drum 5.

The tablets "t" delivered to the back surface inspecting drum 5 are, like the front surface inspecting drum 4, attractively held on the rubber rings 523 mounted on the outer periphery of the outer cylinder 52, and are carried downwardly by the rotation of the outer cylinder 52. At the image pickup point shown in FIG. 6, the back surface image pickup device 8 photographs each tablet "t", to pick up the image of the back surface of the tablet "t". The front and back surface defective decision unit immediately processes the image of the back surface of the tablet "t", to decide the presence or absence of an appearance defect. The decision result is stored in the front and back surface defective decision unit.

If it is decided by the front and back surface detective decision unit that the tablet has an appearance defect on the front or back surface, such a defective table "t" is ejected as follows: namely, when the defective tablet "t'" is carried to the defective table ejection point shown in FIG. 6 by the rotation of the outer cylinder 52, the defective tablet "t'" is excluded from the outer peripheral surface of the outer cylinder 52 and recovered in the defective tablet recovery can 94 through the defective tablet ejection chute 93 by compressed air jetted from the compressed air jetting nozzle 513 disposed in the back surface inspecting drum 5.

If it is decided that the tablet has no appearance defect on both the front and back surfaces, a non-defective tablet passes through the defective tablet ejection point, and at the tablet ejection point shown in FIG. 6, the non-defective tablet is released from the outer peripheral surface of the outer cylinder 52 by compressed air jetted from the compressed air jetting box 512 disposed in the back surface inspecting drum 5. The non-defective tablets are moved onto a non-defective recovery conveyor 92 through the non-defective ejection chute 91 (see FIG. 1), and are carried outside the inspecting apparatus by the conveyor 92 to be thus recovered.

After that, the steps from the step of feeding tablets by the hopper 11 to the step of carrying out non-defective tablets by the non-defective recovery conveyor 92 are continuously repeated. In this way, the side surfaces and front and back surfaces of tablets are continuously inspected by the tablet appearance inspecting apparatus of the present invention.

In addition, the side surface inspecting apparatus and the front and back surface inspecting apparatus of the present invention can be singly used. Alternatively, the side surface inspecting apparatus or the front and back surface inspecting apparatus of the present invention may be combined with a known front and back surface inspecting apparatus or a known side surface inspecting apparatus, to constitute a tablet appearance inspecting apparatus. Further, the configuration of each of the side surface inspecting apparatus and the front and back surface inspecting apparatus can be suitably changed. For example, a simple vibration feeder similar to the vibration feeder 12 used for the tablet feed unit A can be used as the tablet feed portion 61 of the front and back surface inspecting apparatus, and the mechanism for ejecting defective tablets from the side surface inspecting drum 2 or the back surface inspecting drum 5 may be suitably changed. Further, the configuration of each inspecting drum and the mechanism of feeding tablets may be suitably changed without departing from the scope of the present invention.

What is claimed is:

1. An apparatus for inspecting side surfaces of tablets, comprising:

an inner cylinder continuously rotatable at a specific speed;

an outer cylinder disposed on the outer peripheral side of said inner cylinder in such a manner as to be intermittently rotatable along the outer peripheral surface of said inner cylinder, said outer cylinder having in its peripheral wall a number of through-hole shaped holding pockets; and a side surface image pickup device for photographing tablets held in said holding pockets of said outer cylinder, thereby picking up images of the side surfaces of the tablets;

wherein said inspecting apparatus inspects the side surfaces of flat-shaped tablets by holding the tablets, which are in upright states with the diameter direction thereof directed in the vertical direction, in said holding pockets of said outer cylinder intermittently rotating; carrying the tablets by the intermittent rotation of said outer cylinder while making the tablets roll on the outer peripheral surface of said inner cylinder continuously rotating; making, when said outer cylinder is intermittently stopped in the course of carrying operation, the tablets rotate on their axes in said holding pockets by the continuous rotation of said inner cylinder, and photographing the tablets by said side surface image pickup device thereby picking up images of the all-round side surfaces of the tablets; and processing the images thus obtained, thereby detecting the presence or absence of appearance defects on the side surfaces of the tablets.

2. An apparatus for inspecting side surfaces of tablets according to claim 1, wherein said inner cylinder and said outer cylinder are rotatably supported around the outer periphery of a fixed shaft cylinder;

the outer peripheral surface of said inner cylinder has a rail groove formed into a recessed shape in cross-section, said rail groove extending in the circumferential direction in such a manner as to correspond to said holding pockets of said outer cylinder; a number of through-holes are formed in said rail groove in such a manner as to align in the circumferential direction; and at least a pair of rubber rings are mounted on both side edge portions of said rail groove with said through-holes put therebetween, whereby the tablets held in said holding pockets of said outer cylinder are carried while rolling on said rubber rings along said rail groove; and a suction window for sucking the inside of said shaft cylinder is provided in said shaft cylinder at least at a position corresponding to a tablet image pickup point, whereby the inside of said rail groove of said inner cylinder is sucked through said suction window and said through-holes of said inner cylinder, so that the tablets during photographing rotate on their axes in a state being attracted on the outer peripheral surface of said inner cylinder by the suction force.

3. An apparatus for inspecting side surfaces of tablets according to claim 1 or 2, further comprising:

a defective ejecting mechanism for selectively ejecting, in the course of carrying operation, the tablets carried while being held in said holding pockets of said outer cylinder; and a side surface defective decision unit for processing images of the side surfaces of the tablets, thereby deciding the presence or absence of appearance defects;

wherein the tablets, which are decided as defective tablets each having an appearance defect on the side surface by said side surface defective decision unit, are selectively ejected from said holding pockets by said defective ejecting mechanism.

4. An apparatus for inspecting side surfaces of tablets according to claim 3, wherein said defective ejecting mechanism is configured as a compressed air jetting mechanism for jetting compressed air from a compressed air jetting port provided in said shaft cylinder in accordance with the decision result obtained by said side surface defective decision unit, whereby the defective tablets held in said holding pockets are ejected by jetting compressed air from said compressed air jetting port of said shaft cylinder into said holding pockets of said outer cylinder through said through-holes provided in said inner cylinder.

5. An apparatus for inspecting front and back surfaces of tablets comprising:

a front surface inspecting drum for holding flat-shaped tablets, which are in falling-down states with the thickness direction thereof directed in the vertical direction, on the outer peripheral surface thereof, and carrying the tablets by the rotation of said drum at a specific speed;

a back surface inspecting drum, disposed in a state in which the outer peripheral surface thereof is in proximity to the outer peripheral surface of said front surface inspecting drum, for receiving the tablets from said front surface inspecting drum in a state in which the tablets are turned over, holding the tablets, which are in the falling-down states, on the outer peripheral surface thereof, and carrying the tablets by rotation of said drum at a specific speed;

a front surface image pickup device for photographing the tablets held on the outer peripheral surface of said front surface inspecting drum, thereby picking up images of the front surfaces of the tablets;

a back surface image pickup device for photographing the tablets held on the outer peripheral surface of said back surface inspecting drum, thereby picking up images of the back surfaces of the tablets; and a tablet feed unit for feeding the tablets onto the outer peripheral surface of said front surface inspecting drum, said tablet feed unit comprising: a vibration plate having tablet feed passages each having a size allowing a tablet in the falling-down state to pass therethrough, said vibration plate being tilted downwardly to said front inspecting drum by a specific angle with one end of said vibration plate positioned in proximity to the outer peripheral surface of said front surface inspecting drum; and a tablet storing portion for storing a specific amount of tablets, said tablet storing portion being provided on the other end side of said vibration plate, whereby the tablets in said tablet storing portion are continuously introduced in said tablet feed passages of said vibration plate, and the tablets thus introduced in said tablet feed passages are continuously moved, by fine vibration of said vibration plate, to the one end portion of said vibration plate and fed from the one end portion of said vibration plate onto the front surface inspecting drum;

wherein each of said front surface inspecting drum and said back surface inspecting drum includes a suction groove formed in the outer peripheral surface thereof in such a manner as to extend along the circumferential direction, a number of suction holes formed in said suction grooves in such a manner as to align in the circumferential direction, and at least a pair of rubber rings mounted on both side edge portions of said suction groove with said suction holes put therebetween, whereby the tablets are attractively held while lying astride said pair of said rubber rings by a suction force obtained by sucking the inside of said suction groove from the inside of said drum through said suction holes.

6. An apparatus for inspecting front and back surfaces of tablets according to claim 5, wherein said tablet feed unit further comprises a tablet feed roller rotatable at a desired speed, said roller being disposed at the one end of said vibration plate in such a manner as to be in contact with or in proximity to said tablet feed passages, whereby the tablets are moved from the one end portion of said vibration plate onto said front surface inspecting drum by the rotation of said tablet feed roller, to be thereby fed at a desired speed.

7. An apparatus for inspecting front and back surfaces of tablets according to claim 5 or 6, wherein said tablet storing portion of said tablet feed unit comprises:

a turn table rotatable at a specific speed;

an outer chamber formed on said turn table by a ring-like peripheral wall disposed concentrically with the rotational center of said turn table;

an inner chamber formed on said turn table at a position located inside said outer chamber by a ring-like peripheral wall which has a diameter smaller than that of said outer chamber and which is eccentrically from the rotational center of said turn table, the peripheral wall of said inner chamber having at a portion thereof a communication window communicated to said outer chamber; and a communication passage having one end disposed on a portion, inside said outer chamber, of said turn table and the other end communicated to said tablet feed passages of said vibration plate;

wherein the tablets are fed on the portion, in said inner chamber, of said turn table rotating, moved into said outer chamber through said communication window by the centrifugal force, introduced in said communication passage by the rotation of said turn table, and continuously introduced in said tablet feed passages of said vibration plate from said communication passage.

8. An apparatus for inspecting front and back surfaces of tablets according to claim 5, wherein each of said front surface inspecting drum and said back surface inspecting drum comprises:

an inner cylinder having a through-groove extending along the circumferential direction or a number of through-holes aligned along the circumferential direction at least in a tablet carrying range; and an outer cylinder disposed on the outer peripheral side of said inner cylinder and rotatable along the outer peripheral surface of said inner cylinder at a specific speed, said outer cylinder having said suction groove, said suction holes, and said rubber rings;

wherein the inside of said suction groove of said outer cylinder is sucked from the inside of said inner cylinder through said though-groove or through-holes formed in said inner cylinder.

9. An apparatus for inspecting front and back surfaces of tablets according claim 5, further comprising:

a defective ejecting mechanism for selectively ejecting, in the course of carrying operation, the tablets carried while being held on the outer peripheral surface of said back surface inspecting drum; and a front and back surface defective decision unit for processing images of the front and back surfaces of the tablets picked up by said front surface image pickup device and said back surface image pickup device, thereby deciding the presence or absence of appearance defects;

wherein the tablets, which are decided as defective tablets each having an appearance defect on the front surface and/or back surface by said front and back surface defective decision unit, are selectively ejected from said back surface inspecting drum by said defective ejecting mechanism.

10. An apparatus for inspecting front and back surfaces of tablets according to claim 9, wherein said defective ejecting mechanism is configured as a compressed air jetting mechanism for jetting compressed air from a compressed air jetting portion provided in said back surface inspecting drum in accordance with the decision result obtained by said front and back surface defective decision unit, whereby the defective tablets, which are carried to the defective ejection point while being held on the outer peripheral surface of said back surface inspecting drum, are selectively ejected from the outer peripheral surface of said back surface inspecting drum by jetting compressed air from said compressed air jetting portion into said suction groove of said back surface inspecting drum.

11. A tablet appearance inspecting apparatus comprising a side inspecting unit and a front and back surface inspecting unit, said side inspecting unit comprising:

an inner cylinder continuously rotatable at a specific speed;

an outer cylinder disposed on the outer peripheral side of said inner cylinder in such a manner as to be intermittently rotatable along the outer peripheral surface of said inner cylinder, said outer cylinder having in its peripheral wall a number of through-hole shaped holding pockets; and a side surface image pickup device for photographing tablets held in said holding pockets of said outer cylinder, thereby picking up images of the side surfaces of the tablets;

wherein said inspecting apparatus inspects the side surfaces of flat-shaped tablets by holding the tablets, which are in upright states with the diameter direction thereof directed in the vertical direction, in said holding pockets of said outer cylinder intermittently rotating;

carrying the tablets by the intermittent rotation of said outer cylinder while making the tablets roll on the outer peripheral surface of said inner cylinder continuously rotating; making, when said outer cylinder is intermittently stopped in the course of carrying operation, the tablets rotate on their axes in said holding pockets by the continuous rotation of said inner cylinder, and photographing the tablets by said side surface image pickup device thereby picking up images of the all-round side surfaces of the tablets; and processing the images thus obtained, thereby detecting the presence or absence of appearance defects on the side surfaces of the tablets;

said front and back surface inspecting unit comprising:

a front surface inspecting drum for holding flat-shaped tablets, which are in falling-down states with the thickness direction thereof directed in the vertical direction, on the outer peripheral surface thereof, and carrying the tablets by the rotation of said drum at a specific speed;

a back surface inspecting drum, disposed in a state in which the outer peripheral surface thereof is in proximity to the outer peripheral surface of said front surface inspecting drum, for receiving the tablets from said front surface inspecting drum in a state in which the tablets are turned over, holding the tablets, which are in the falling-down states, on the outer peripheral surface thereof, and carrying the tablets by rotation of said drum at a specific speed;

a front surface image pickup device for photographing the tablets held on the outer peripheral surface of said front surface inspecting drum, thereby picking up images of the front surfaces of the tablets;

a back surface image pickup device for photographing the tablets held on the outer peripheral surface of said back surface inspecting drum, thereby picking up images of the back surfaces of the tablets; and a tablet feed unit for feeding the tablets onto the outer peripheral surface of said front surface inspecting drum, said tablet feed unit comprising: a vibration plate having tablet feed passages each having a size allowing a tablet in the falling-down state to pass therethrough, said vibration plate being tilted downwardly to said front inspecting drum by a specific angle with one end of said vibration plate positioned in proximity to the outer peripheral surface of said front surface inspecting drum; and a tablet storing portion for storing a specific amount of tablets, said tablet storing portion being provided on the other end side of said vibration plate, whereby the tablets in said tablet storing portion are continuously introduced in said tablet feed passages of said vibration plate, and the tablets thus introduced in said tablet feed passages are continuously moved, by fine vibration of said vibration plate, to the one end portion of said vibration plate and fed from the one end portion of said vibration plate onto the front surface inspecting drum;

wherein each of said front surface inspecting drum and said back surface inspecting drum includes a suction groove formed in the outer peripheral surface thereof in such a manner as to extend along the circumferential direction, a number of suction holes formed in said suction grooves in such a manner as to align in the circumferential direction, and at least a pair of rubber rings mounted on both side edge portions of said suction groove with said suction holes put therebetween, whereby the tablets are attractively held while lying astride said pair of said rubber rings by a suction force obtained by sucking the inside of said suction groove from the inside of said drum through said suction holes;

said tablet appearance inspecting apparatus being operated to inspect side surfaces of tablets by said side surface inspecting unit and selectively eject defective tablets each having an appearance defect on the side surface; feed all of the tablets with no defects on the side surfaces from said side surface inspecting drum into said tablet storing portion of said front and back inspecting unit; inspect front and back surfaces of the tablets by said front and back surface inspecting unit and selectively eject defective tablets each having an appearance defect on the front or back surface; and recover non-defective tablets with no appearance defects on the side surfaces and front and back surfaces from said back surface inspecting drum of said front and back surface inspecting unit.

12. A tablet appearance inspecting apparatus according to claim 11, wherein said apparatus is operated to feed tablets to be inspected in said tablet storing portion of said front and back surface inspecting unit; inspect the front and back surfaces of the tablets by said front and back surface inspecting unit, and selectively eject defective tablets each having an appearance defect on the front or back surface; change the postures of all of the tablets with no appearance defects on the front and back surfaces from the falling-down postures to upright postures, and feed the tablets from said back surface inspecting drum of said front and back surface inspecting unit onto said side surface inspecting drum of said side surface inspecting unit; inspect the side surfaces of the tablets by said side surface inspecting unit and selectively eject defective tablets each having an appearance defect on the side surface; and recover non-defective tablets with no appearance defects on the side surfaces and front and back surfaces from said side surface inspecting drum of said side surface inspecting unit.

13. A tablet appearance inspecting apparatus according to claim 11 or 12, wherein said inner cylinder and said outer cylinder are rotatably supported around the outer periphery of a fixed shaft cylinder;

the outer peripheral surface of said inner cylinder has a rail groove formed into a recessed shape in cross-section, said rail groove extending in the circumferential direction in such a manner as to correspond to said holding pockets of said outer cylinder; a number of through-holes are formed in said rail groove in such a manner as to align in the circumferential direction; and at least a pair of rubber rings are mounted on both side edge portions of said rail groove with said through-holes put therebetween, whereby the tablets held in said holding pockets of said outer cylinder are carried while rolling on said rubber rings along said rail groove; and a suction window for sucking the inside of said shaft cylinder is provided in said shaft cylinder at least at a position corresponding to a tablet image pickup point, whereby the inside of said rail groove of said inner cylinder is sucked through said suction window and said through-holes of said inner cylinder, so that the tablets during photographing rotate on their axes in a state being attracted on the outer peripheral surface of said inner cylinder by the suction force.

14. A tablet appearance inspecting apparatus according to claim 11, further comprising:

a defective ejecting mechanism for selectively ejecting, in the course of carrying operation, the tablets carried while being held in said holding pockets of said outer cylinder; and a side surface defective decision unit for processing images of the side surfaces of the tablets, thereby deciding the presence or absence of appearance defects;

wherein the tablets, which are decided as defective tablets each having an appearance defect on the side surface by said side surface defective decision unit, are selectively ejected from said holding pockets by said defective ejecting mechanism.

15. An apparatus for inspecting side surfaces of tablets according to claim 14, wherein said defective ejecting mechanism is configured as a compressed air jetting mechanism for jetting compressed air from a compressed air jetting port provided in said shaft cylinder in accordance with the decision result obtained by said side surface defective decision unit, whereby the defective tablets held in said holding pockets are ejected by jetting compressed air from said compressed air jetting port of said shaft cylinder into said holding pockets of said outer cylinder through said through-holes provided in said inner cylinder.

16. A tablet appearance inspecting apparatus according to claim 11 or 12, wherein said tablet feed unit further comprises a tablet feed roller rotatable at a desired speed, said roller being disposed at the one end of said vibration plate in such a manner as to be in contact with or in proximity to said tablet feed passages, whereby the tablets are moved from the one end portion of said vibration plate onto said front surface inspecting drum by the rotation of said tablet feed roller, to be thereby fed at a desired speed.

17. A table appearance inspecting apparatus according to claim 11, wherein said tablet storing portion of said tablet feed unit comprises:

a turn table rotatable at a specific speed;

an outer chamber formed on said turn table by a ring-like peripheral wall disposed concentrically with the rotational center of said turn table;

an inner chamber formed on said turn table at a position located inside said outer chamber by a ring-like peripheral wall which has a diameter smaller than that of said outer chamber and which is eccentrically from the rotational center of said turn table, the peripheral wall of said inner chamber having at a portion thereof a communication window communicated to said outer chamber; and a communication passage having one end disposed on a portion, inside said outer chamber, of said turn table and the other end communicated to said tablet feed passages of said vibration plate;

wherein the tablets are fed on the portion, in said inner chamber, of said turn table rotating, moved into said outer chamber through said communication window by the centrifugal force, introduced in said communication passage by the rotation of said turn table, and continuously introduced in said tablet feed passages of said vibration plate from said communication passage.

18. A tablet appearance inspecting apparatus according to claim 11, wherein each of said front surface inspecting drum and said back surface inspecting drum comprises:

an inner cylinder having a through-groove extending along the circumferential direction or a number of through-holes aligned along the circumferential direction at least in a tablet carrying range; and an outer cylinder disposed on the outer peripheral side of said inner cylinder and rotatable along the outer peripheral surface of said inner cylinder at a specific speed, said outer cylinder having said suction groove, said suction holes, and said rubber rings;

wherein the inside of said suction groove of said outer cylinder is sucked from the inside of said inner cylinder through said though-groove or through-holes formed in said inner cylinder.

19. A tablet appearance inspecting apparatus according to claim 11, further comprising:

a defective ejecting mechanism for selectively ejecting, in the course of carrying operation, the tablets carried while being held on the outer peripheral surface of said back surface inspecting drum; and a front and back surface defective decision unit for processing images of the front and back surfaces of the tablets picked up by said front surface image pickup device and said back surface image pickup device, thereby deciding the presence or absence of appearance defects;

wherein the tablets, which are decided as defective tablets each having an appearance defect on the front surface and/or back surface by said front and back surface defective decision unit, are selectively ejected from said back surface inspecting drum by said defective ejecting mechanism.

20. A tablet appearance inspecting apparatus according to claim 19, wherein said defective ejecting mechanism is configured as a compressed air jetting mechanism for jetting compressed air from a compressed air jetting portion provided in said back surface inspecting drum in accordance with the decision result obtained by said front and back surface defective decision unit, whereby the defective tablets, which are carried to the defective ejection point while being held on the outer peripheral surface of said back surface inspecting drum, are selectively ejected from the outer peripheral surface of said back surface inspecting drum by jetting compressed air from said compressed air jetting portion into said suction groove of said back surface inspecting drum.

* * * * *